(12) United States Patent
Sependa et al.

(10) Patent No.: US 7,625,910 B2
(45) Date of Patent: Dec. 1, 2009

(54) CO-CRYSTAL

(75) Inventors: George Joseph Sependa, Cheshire (GB); Richard Storey, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/748,651

(22) Filed: May 15, 2007

(65) Prior Publication Data

US 2008/0045481 A1    Feb. 21, 2008

(30) Foreign Application Priority Data

May 16, 2006    (GB)    ................... 0609621.8

(51) Int. Cl.
*A61K 31/517*    (2006.01)
(52) U.S. Cl. .................. 514/266.23; 544/244
(58) Field of Classification Search .................. 544/244
See application file for complete search history.

(56) References Cited

U.S. PATENT DOCUMENTS

2006/0116357 A1*    6/2006    Heron et al. ................... 514/80

FOREIGN PATENT DOCUMENTS

WO    2004/058781 A1    7/2004

OTHER PUBLICATIONS

Berge et al. Pharmaceutical Salts, 1977, Journal of Pharmaceutical Sciences, 66, 1-19.*

* cited by examiner

*Primary Examiner*—James O Wilson
*Assistant Examiner*—Brian McDowell

(57) ABSTRACT

The present invention relates to a novel co-crystal of 2-{ethyl [3-({4-[(5-{2-[(3-fluorophenyl)amino]-2-oxoethyl}-1H-pyrazol-3-yl)amino]quinazolin-7-yl}oxy)propyl] amino}ethyl dihydrogen phosphate (AZD1152) which is an aurora kinase inhibitor that is useful in the treatment of hyperproliferative diseases such as cancer.

6 Claims, 7 Drawing Sheets

DVS Isotherm Plot

CO-CRYSTAL

This application claims the benefit under 35 U.S.C. § 119 (a)-(d) of Application No. GB 0609621.8 filed on May 16, 2006.

The present invention relates to a novel co-crystal and more particularly to a novel co-crystal form of 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate (herein referred to as AZD1152) which is an aurora kinase inhibitor that is useful in the treatment of hyperproliferative diseases such as cancer. More specifically the invention relates to a maleate co-crystal of AZD1152, to a process for the preparation of a maleate co-crystal of AZD1152, to pharmaceutical compositions containing a maleate co-crystal of AZD1152, to the use of a maleate co-crystal of AZD1152 in the manufacture of a medicament for the treatment of hyperproliferative diseases such as cancer, and to methods of treating hyperproliferative diseases such as cancer in the human or animal body by administering a therapeutically effective amount of a maleate co-crystal of AZD1152. This invention also relates to a particular crystalline form of a maleate co-crystal of AZD1152.

Cancer (and other hyperproliferative diseases) is characterised by uncontrolled cellular proliferation which occurs when the normal regulation of cell proliferation is lost. This loss often appears to be the result of genetic damage to the cellular pathways that control a cell's progress through its cell cycle.

In eukaryotes, an ordered cascade of protein phosphorylation is thought to control the cell cycle. Several families of protein kinases that play critical roles in this cascade have been identified. The activity of many of these kinases is increased in human tumours when compared to normal tissue. This can occur by either increased levels of expression of the protein (for example as a result of gene amplification), or by changes in expression of co activators or inhibitory proteins.

The first identified, and most widely studied of these cell cycle regulators are the cyclin dependent kinases (or CDKs). More recently, protein kinases that are structurally distinct from the CDK family have been identified and found to play critical roles in regulating the cell cycle. These kinases also appear to be important in oncogenesis and include human homologues of the *Drosophila* aurora and *S. cerevisiae* Ipl1 proteins. The three human homologues of these genes aurora-A, aurora-B and aurora-C (also known as aurora2, aurora1 and aurora3 respectively) encode cell cycle regulated serine-threonine protein kinases (summarised in Adams et al., 2001, Trends in Cell Biology. 11(2): 49-54). These show a peak of expression and kinase activity through G2 and mitosis. Several observations implicate the involvement of human aurora proteins in cancer. The aurora-A gene maps to chromosome 20q13, a region that is frequently amplified in human tumours including both breast and colon tumours. Aurora-A may be the major target gene of this amplicon, since aurora-A DNA is amplified and mRNA overexpressed in greater than 50% of primary human colorectal cancers. In these tumours aurora-A protein levels appear greatly elevated compared to adjacent normal tissue. In addition, transfection of rodent fibroblasts with human aurora-A leads to transformation, conferring the ability to grow in soft agar and form tumours in nude mice (Bischoff et al., 1998, The EMBO Journal. 17(11): 3052-3065). Other work (Zhou et al., 1998, Nature Genetics. 20(2): 189-93) has shown that artificial over-expression of aurora-A leads to an increase in centrosome number and an increase in aneuploidy, a known event in the development of cancer.

It has also been shown that there is an increase in expression of aurora-B (Adams et al., 2001, Chromsoma. 110(2): 65-74) and aurora-C (Kimura et al., 1999, Journal of Biological Chemistry, 274(11): 7334-40) in tumour cells when compared to normal cells. Aurora-B is over-expressed in cancer cells and increased levels of aurora-B have been shown to correlate with advanced stages of colorectal cancer (Katayama et al (1999) J. Natl. Cancer Inst. 91:1160). Furthermore, one report suggests that overexpression of aurora-B induces aneuploidy through increased phosphorylation of histone H3 at serine 10 and that cells over-expressing aurora-B form more aggressive tumours that develop metastases (Ota, T. et al, 2002, Cancer Res. 62: 5168-5177). Aurora-B is a chromosome passenger protein which exists in a stable complex with at least three other passenger proteins, Survivin, INCENP and Borealin (Carmena M. et al. 2003, Nat. Rev. Mol. Cell Biol. 4: 842-854). Survivin is also up-regulated in cancer and contains a BIR (Baculovirus Inhibitor of apoptosis protein (IAP) Repeat) domain and may therefore play a role in protecting tumour cells from apoptosis and/or mitotic catastrophe.

With regard to aurora-C, its expression is thought to be restricted to the testis but it has been found to be over-expressed in various cancer lines. (Katayama H et al, 2003, Cancer and Metastasis Reviews 22: 451-464).

Importantly, it has also been demonstrated that abrogation of aurora-A expression and function by antisense oligonucleotide treatment of human tumour cell lines (WO 97/22702 and WO 99/37788) leads to cell cycle arrest and exerts an antiproliferative effect in these tumour cell lines. Additionally, small molecule inhibitors of aurora-A and aurora-B have been demonstrated to have an antiproliferative effect in human tumour cells (Keen et al. 2001, Poster #2455, American Association of Cancer Research annual meeting), as has selective abrogation of aurora-B expression alone by siRNA treatment (Ditchfield et al. 2003, Journal of Cell Biology, 161(2): 267-280). This indicates that inhibition of the function of aurora-A and/or aurora-B will have an antiproliferative effect that may be useful in the treatment of human tumours and other hyperproliferative disease. The inhibition of aurora kinases as a therapeutic approach to these diseases may have significant advantages over targeting signalling pathways upstream of the cell cycle (e.g. those activated by growth factor receptor tyrosine kinases such as epidermal growth factor receptor (EGFR) or other receptors). Since the cell cycle is ultimately downstream of all of these diverse signalling events, cell cycle directed therapies such as inhibition of aurora kinases would be predicted to be active across all proliferating tumour cells, whilst approaches directed at specific signalling molecules (e.g. EGFR) would be predicted to be active only in the subset of tumour cells which express those receptors. It is also believed that significant "cross talk" exists between these signalling pathways meaning that inhibition of one component may be compensated for by another.

Inhibitors of the aurora kinases are described in International Patent Applications WO 03/55491 and WO 2004/058781, and in particular WO 2004/058781 discloses a compound which possesses the following structural formula, referred to herein as AZD1152:

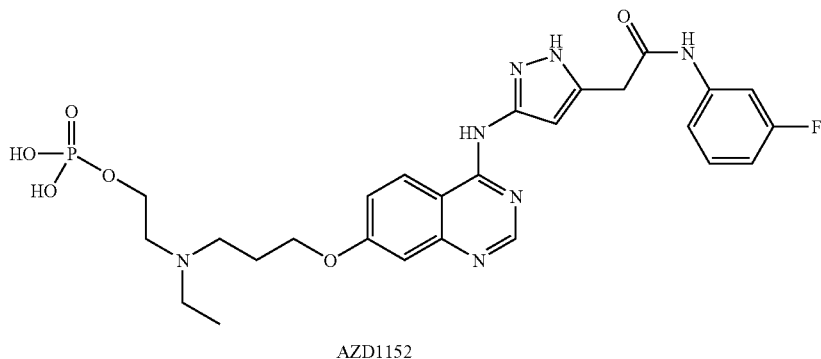

AZD1152

AZD1152 is a pro-drug that is rapidly and completely converted (in human plasma) to the active moiety referred to herein as AZD1152 HQPA:

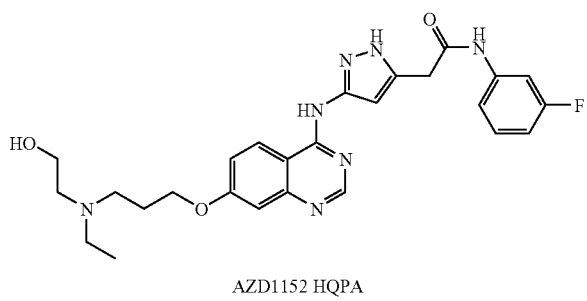

AZD1152 HQPA

AZD1152 HQPA is an ATP-competitive and reversible inhibitor of the aurora kinases with potent activity against aurora A, B-INCENP and C-INCENP (Ki's 1369±419.2 nM, 0.359±0.386 nM and 17.03±12.2 nM respectively). AZD1152 has been found to inhibit tumour growth in a panel of human colorectal (SW620, HCT116, Colo205) and lung (A549, Calu-6) tumour xenografts with statistical significance.

AZD1152 is disclosed in WO 2004/058781 as the dihydrochloride salt and also as the free base in hydrated forms. In particular the free form is disclosed in the trihydrate to tetrahydrate form.

From a manufacturing perspective, hydrated forms are problematic as they require controls to be in place during manufacture, drying, storage and processing. In addition, obtaining and maintaining a sample of compound with a consistent stoichiometric compound to water ratio is difficult. In the case of the previously disclosed forms of AZD1152, and in particular with the free form, water molecules are only loosely bound to each molecule of AZD152, so the extent of association and disassociation of water molecules to the AZD1152 drug varies greatly with temperature and relative humidity. Therefore, for a given weight of AZD1152, the actual amount of AZD1152 in terms of number of molecules of AZD1152 will depend upon the temperature and relative humidity as the water content will vary. The effectiveness of any dose determined by weight is thus also dependent on the temperature and relative humidity to which it is exposed. Dynamic Vapour Sorption has been used to measure the variation in the level of water associated with AZD1152 with humidity.

WO 2004/058781 discloses, in general terms, certain pharmaceutically acceptable salts of the compounds disclosed therein. AZD1152 is only disclosed as the dihydrochloride salt and as the free form. No other forms of AZD1152 are mentioned. In particular, WO 2004/058781 does not disclose any other co-crystal of AZD1152 and it certainly does not consider whether any particular co-crystals of particular compounds would possess surprising benefits and particularly not benefits that might ameliorate the problems discussed herein.

Unexpectedly and surprisingly we have found that the maleate co-crystal of AZD1152 exists in an anhydrous form, which is substantially non-hygroscopic. Furthermore, although the stoichiometric ratio of drug to maleate may vary within a range of, for example, 0.8:1 to 1.2:1, or 0.9:1 to 1.1:1, we have found that the maleate co-crystal of AZD1152 disclosed herein has a reproducible stoichiometric ratio of drug to maleate of substantially 1:1. The effectiveness of a weight dose of AZD1152 maleate co-crystal is therefore affected by temperature and relative humidity to a much lesser extent than that of the free form, the dihydrochloride salt and other co-crystal forms of AZD1152 that have been evaluated. Additionally, the maleate co-crystal of AZD1152 is easier to manufacture as there is less need to control the humidity levels in the manufacturing process. The anhydrous nature of the maleate co-crystal further means that it will be possible to formulate it using limited aqueous conditions and/or high temperature environments because of the lower risk of hydration/dehydration during processing conditions that use aqueous environments e.g. wet granulation.

Additionally, we have discovered that a maleate co-crystal of AZD1152 surprisingly contains fewer impurities than the free form. In particular, it appears that certain recalcitrant impurities that are present in the free form are surprisingly present to a much lesser extent after conversion of the free form into the maleate form.

Accordingly, the present invention provides a maleate co-crystal of AZD1152.

For the avoidance of doubt, the terms "maleate co-crystal of AZD1152", "AZD1152 maleate co-crystal" or "AZD1152 maleate" (or any other similar term used herein) refer to all forms of association between AZD1152 and maleic acid, including salt forms. In particular, these terms encompass:

(i) a non-ionic association between the AZD1152 and maleic acid (i.e. where no proton transfer has occurred between the drug and the maleic acid); or (ii) an ionic interaction where proton transfer between the AZD1152 and maleic acid has occurred to form a maleate salt of AZD1152, or (iii) mixtures of (i) and (ii) above.

In a particular embodiment of the invention, the maleate co-crystal comprises is a non-ionic association between the AZD1152 drug and the maleic acid (i.e. where no proton transfer has occurred between the drug and the maleic acid).

In an alternative embodiment of the invention, the maleate co-crystal is a maleate salt of AZD1152.

In a particular embodiment, a maleate co-crystal of AZD1152 is formed by mixing AZD1152 free form with maleic acid in a suitable solvent such as methanol, dimethyl sulphoxide (DMSO) or a mixture of DMSO with methanol, acetonitrile, and other similar solvents. The maleate co-crystal may be isolated by allowing crystallisation to occur and then isolating the resultant crystalline material. The identity of a maleate co-crystal of AZ1152 of the present invention can be confirmed by proton nuclear magnetic resonance (NMR) analysis.

It should also be understood that a compound or co-crystal of the invention may exhibit the phenomenon of tautomerism and that the formulae drawings within this specification can represent only one of the possible tautomeric forms. It is to be understood that the invention encompasses any tautomeric form which has Aurora kinase inhibitory activity and in particular Aurora-A and/or Aurora-B kinase inhibitory activity and is not to be limited merely to any one tautomeric form utilised within the formulae drawings.

The present invention also relates to a particular crystalline form of the maleate co-crystal of AZD1152. This crystalline form is prepared by crystallising the maleate crystal of AZD1152 from an organic solvent such as a mixture of methanol and dimethyl sulphoxide (DMSO). Further experimental details are provided in the Examples.

Accordingly, the invention provides a crystalline form of the maleate co-crystal of AZD1152.

The crystalline form of the maleate co-crystal of AZD1152 is characterised in that it provides an X-ray powder diffraction pattern substantially as shown in FIG. 1.

The most prominent X-ray powder diffraction peaks for the crystalline form of the maleate co-crystal of AZD1152 are shown in table 1:

TABLE 1

| Angle 2-Theta° | Relative Intensity % |
| --- | --- |
| 5.118 | 100 |
| 6.446 | 18.8 |
| 8.158 | 28.1 |
| 10.171 | 13.1 |
| 11.917 | 5.9 |
| 12.861 | 18 |
| 13.849 | 48.3 |
| 14.909 | 25.2 |
| 15.234 | 36 |
| 15.738 | 27.6 |
| 16.506 | 18.8 |
| 16.884 | 23 |
| 17.232 | 42.5 |
| 18.134 | 13.8 |
| 19.327 | 62.7 |
| 19.82 | 38.8 |
| 20.082 | 61 |
| 20.582 | 61.4 |
| 21.008 | 32 |
| 21.663 | 87.3 |
| 22.425 | 18.8 |
| 23.228 | 26.8 |

TABLE 1-continued

| Angle 2-Theta° | Relative Intensity % |
| --- | --- |
| 23.583 | 37.7 |
| 23.994 | 25.7 |
| 24.271 | 24.1 |
| 24.671 | 23.3 |
| 25.32 | 19.1 |
| 25.574 | 32.9 |
| 25.813 | 43.8 |
| 26.21 | 35.3 |
| 27.122 | 16 |
| 27.946 | 45.4 |
| 28.418 | 31.6 |
| 28.847 | 21.7 |
| 29.725 | 26.1 |
| 30.521 | 18.8 |
| 31.74 | 15.4 |
| 33.424 | 14.7 |
| 36.181 | 15.3 |
| 38.106 | 10.8 |

According to the present invention there is provided a crystalline form of the maleate co-crystal of AZD1152, wherein said co-crystal has an X-ray powder diffraction pattern with at least one specific peak at about 2-theta=15.2°.

According to the present invention there is provided a crystalline form of the maleate co-crystal of AZD1152, wherein said co-crystal has an X-ray powder diffraction pattern with specific peaks at about 2-theta=12.9°.

According to the present invention there is provided a crystalline form of the maleate co-crystal of AZD1152, wherein said co-crystal has an X-ray powder diffraction pattern with specific peaks at about 2-theta=15.2 or 10.2°.

According to the present invention there is provided a crystalline form of the maleate co-crystal of AZD1152, wherein said co-crystal has an X-ray powder diffraction pattern with specific peaks at about 2-theta=18.1°.

According to the present invention there is provided a crystalline form of the maleate co-crystal of AZD1152, wherein said co-crystal has an X-ray powder diffraction pattern with at least one specific peak at about 2-theta=10.2°, 12.9°, 15.2° or 18.1°.

According to the present invention there is provided a crystalline form of the maleate co-crystal of AZD1152, wherein said co-crystal has an X-ray powder diffraction pattern with specific peaks at about 2-theta=12.9° and 15.2° and/or 10.2°.

According to the present invention there is provided a crystalline form of the maleate co-crystal of AZD1152, wherein said co-crystal has an X-ray powder diffraction pattern with specific peaks at about 2-theta=10.2°, 12.9°, 15.2° and 18.1°.

According to the present invention there is provided a crystalline form of the maleate co-crystal of AZD1152, wherein said co-crystal has an X-ray powder diffraction pattern with specific peaks at about any one of or combination of the 2-theta ° values shown in table 1.

According to the present invention there is provided a crystalline form of the maleate co-crystal of AZD1152, wherein said co-crystal has an X-ray powder diffraction pattern substantially the same as the X-ray powder diffraction pattern shown in FIG. 1.

When it is stated herein that the present invention relates to a crystalline form of the maleate co-crystal of AZD1152, the degree of crystallinity as determined by X-ray powder diffraction data is conveniently greater than about 60%, more conveniently greater than about 80%, preferably greater than about 90%.

In the preceding paragraphs defining the X-ray powder diffraction peaks for the crystalline forms of the maleate co-crystal of AZD1152, the term "at about" is used in the expression " . . . at about 2-theta= . . . " to indicate that the precise position of peaks (i.e. the recited 2-theta angle values) should not be construed as being absolute values because, as will be appreciated by those skilled in the art, the precise position of the peaks may vary slightly between one machine and another, from one sample to another, or as a result of slight variations in measurement conditions utilised. It is also stated in the preceding paragraphs that the crystalline forms of the maleate co-crystal of AZD1152 provide X-ray powder diffraction patterns 'substantially' the same as the X-ray powder diffraction patterns shown in FIG. 1, and have substantially the most prominent peaks (2-theta angle values) shown in Table 1 and in particular at about 2-theta=10.2°, 12.9°, 15.2° or 18.1°. It shall be appreciated that the use of the term 'substantially' in this context is also intended to indicate that the 2-theta angle values of the X-ray powder diffraction patterns may vary slightly from one machine to another, from one sample to another, or as a result of slight variations in measurement conditions utilised, so the peak positions shown in the Figure or quoted in the Table are again not to be construed as absolute values.

In this regard, it is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996). Therefore, it shall be understood that the crystalline form of the maleate co-crystal of AZD1152 of the present invention is not limited to the crystals that provide X-ray powder diffraction patterns identical to the X-ray powder diffraction patterns shown in FIG. 1 and any crystals providing X-ray powder diffraction patterns substantially the same as that shown in FIG. 1 fall within the scope of the present invention. A person skilled in the art of X-ray powder diffraction is able to judge the substantial identity of X-ray powder diffraction patterns.

Generally, a measurement error of a diffraction angle in an X-ray powder diffractogram is about 2-theta=0.5° or less (or, more suitably, about 2-theta=0.2° or less) and such degree of a measurement error should be taken into account when considering the X-ray powder diffraction pattern in FIG. 1, and when interpreting the peak positions referred to in the text above and in Table 1. Therefore, where it is stated, for example, that the co-crystal has an X-ray powder diffraction pattern with at least one specific peak at about 2-theta=15.2° (or any one of the other angles mentioned above) then this can be interpreted as being 2-theta=15.2° plus or minus 0.5°, or 2-theta=15.2° plus or minus 0.2°.

According to another aspect of the invention, there is provided a method of preparing a maleate co-crystal of AZD1152 as herein defined, said method comprising the step of mixing a solution of AZD1152 free form with maleic acid in a suitable solvent such as methanol, N-methyl-2-pyrrolidinone, dimethyl sulphoxide (DMSO) or a mixture of DMSO with methanol, acetonitrile, and other similar solvents. The method may further comprise the steps of crystallisation and, optionally, isolation of the crystalline maleate co-crystal of AZD1152 thus formed.

The process may additionally comprise the further steps of washing the maleate co-crystal of AZD1152 with a suitable solvent; and drying the maleate co-crystal of AZD1152.

Suitably, AZD1152 free form is dissolved in a suitable solvent (such as dimethylsulfoxide, methanol, a mixture thereof or N-methyl-2-pyrrolidinone) and generally mixed with a solution of maleic acid (which is dissolved in either the same or a compatible solvent). Alternatively solid maleic acid may be added to the AZD1152 free form solution (or vice versa, i.e. the AZD1152 free form solution may be added to the solid maleic acid). Suitably, the solution is stirred to facilitate mixing of the AZD1152 free form and the added maleic acid. The materials (ideally but not exclusively in a 1:1 ratio) may be mixed at ambient temperature although the procedure may also be performed at higher temperatures.

Any suitable method known in the art for isolating the crystalline maleate form of AZD1152 may be used. Suitably, the maleate co-crystal of AZD1152 is collected by filtration.

Preferably the washed maleate co-crystal of AZD1152 is dried under vacuum.

In general, a ratio of AZD1152 free form:maleic acid of 1:1 is desired. This desired 1:1 ratio can be obtained by mixing the AZD1152 free form and maleic acid at compositions anywhere within the range of 0.6-1.4 AZD1152 free form:1.0 maleic acid. Suitably, the ratio of AZD1152 free form:maleic acid in the mixture is within the range of 0.9-1.1 and particularly 1.0-1.1 AZD1152 free form:1.0-1.1 maleic acid. Generally an excess of maleic acid should be used and in particular the ratio of AZD1152 free form:maleic acid in the mixture is within the range of 0.6-1.0 and particularly 0.9-1.0 AZD1152 free form:1.0 maleic acid.

AZD1152 maleate co-crystal typically self crystallise, but it will be appreciated by a person skilled in the art that seeding may be used if required or desired in order to promote co-crystal formation.

According to a further aspect of the invention there is provided a pharmaceutical composition which comprises a maleate co-crystal of AZD1152, as defined herein in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, soya bean oil, coconut oil, or preferably olive oil, or any other acceptable vehicle.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible or lyophilised powders and granules suitable for preparation of an aqueous suspension or solution by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, solutions, emulsions or particular systems, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in polyethylene glycol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30 µm or much less preferably 5 µm or less and more preferably between 5 µm and 1 µm, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

Therefore in a further aspect of the invention there is provided a maleate co-crystal of AZD1152 for use in therapy. Further provided is a maleate co-crystal of AZD1152 for use as a medicament. Another aspect of the invention provides a maleate co-crystal of AZD1152 for use as a medicament for the treatment of hyperproliferative diseases such as cancer and in particular colorectal, breast, lung, prostate, bladder, renal or pancreatic cancer or leukaemia or lymphoma. The leukaemias and lymphomas mentioned herein maybe tumours of myeloid lineage such as acute myeloid leukaemia or of lymphoid lineage.

Additionally a maleate co-crystal of AZD1152 is provided for use in a method of treatment of a warm-blooded animal such as man by therapy. Another aspect of the invention provides a maleate co-crystal of AZD1152 for use in a method of treatment of hyperproliferative diseases such as cancer and in particular colorectal, breast, lung, prostate, bladder, renal or pancreatic cancer or leukaemia or lymphoma.

In another aspect of the invention, there is provided the use of a maleate co-crystal of AZD1152 in the preparation of a medicament for the treatment of a disease where the inhibition of one or more aurora kinase(s) is beneficial. In particular it is envisaged that inhibition of aurora A kinase and/or aurora B kinase may be beneficial. Preferably inhibition of aurora B kinase is beneficial. In another aspect of the invention, there is provided the use of a maleate co-crystal of AZD1152 in the preparation of a medicament for the treatment of hyperproliferative diseases such as cancer and in particular colorectal, breast, lung, prostate, bladder, renal or pancreatic cancer or leukaemia or lymphoma.

According to yet another aspect, there is provided a maleate co-crystal of AZD1152 for use in the method of treating a human suffering from a disease in which the inhibition of one or more aurora kinase is beneficial, comprising the steps of administering to a person in need thereof a therapeutically effective amount of a maleate co-crystal of AZD1152. In particular it is envisaged that inhibition of aurora A kinase and/or aurora B kinase may be beneficial. Preferably inhibition of aurora B kinase is beneficial. Further provided is a maleate co-crystal of AZD1152 for use in the method of treating a human suffering from a hyperproliferative disease such as cancer and in particular colorectal, breast, lung, prostate, bladder, renal or pancreatic cancer or leukaemia or lymphoma, comprising the steps of administering to a person in need thereof a therapeutically effective amount of a maleate co-crystal of AZD1152. The use of a maleate co-crystal of AZD1152 in any of the methods of treating a human described above also form aspects of this invention.

For the above mentioned therapeutic uses the dose administered will vary with the compound employed, the mode of administration, the treatment desired, the disorder indicated and the age and sex of the animal or patient. The size of the dose would thus be calculated according to well known principles of medicine.

In using a maleate co-crystal of AZD1152 for therapeutic or prophylactic purposes it will generally be administered so that a daily dose in the range, for example, 0.05 mg/kg to 50 mg/kg body weight is received, given if required in divided doses. In general lower doses will be administered when a parenteral route is employed. Thus, for example, for intravenous administration, a dose in the range, for example, 0.05 mg/kg to 25 mg/kg body weight will generally be used. Similarly, for administration by inhalation, a dose in the range, for example, 0.05 mg/kg to 25 mg/kg body weight will be used.

The treatment defined herein may be applied as a sole therapy or may involve, in addition to the compound of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestratrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine-threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In addition a maleate co-crystal of AZD1152 may be used in combination with one or more cell cycle inhibitors. In particular with cell cycle inhibitors which inhibit bub1, bubR1 or CDK.

Such conjoint treatment may be achieved by way of the simultaneous, sequential or separate dosing of the individual components of the treatment. Such combination products employ the compounds of this invention within the dosage range described herein and the other pharmaceutically-active agent within its approved dosage range.

According to an aspect of the invention there is provided a combination suitable for use in the treatment of cell proliferative disorders (such as cancer) comprising a maleate co-crystal of AZD1152 as defined hereinbefore and an additional anti-tumour agent as defined hereinbefore.

According to this aspect of the invention there is provided a pharmaceutical product comprising a maleate co-crystal of AZD1152 as defined hereinbefore and an additional anti-tumour agent as defined hereinbefore for the conjoint treatment of cell proliferative disorders (such as cancer).

In addition to their use in therapeutic medicine, a maleate co-crystal of AZD1152 are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

The maleate co-crystal (s) of the invention inhibit the serine-threonine kinase activity of the aurora kinases, in particular aurora A kinase and/or aurora B kinase and thus inhibit the cell cycle and cell proliferation. Compounds which inhibit aurora B kinase are of particular interest. These properties may be assessed for example, using one or more of the procedures set out below.

(a) In Vitro Aurora A Kinase Inhibition Test

This assay determines the ability of a test compound to inhibit serine-threonine kinase activity. DNA encoding aurora A may be obtained by total gene synthesis or by cloning. This DNA may then be expressed in a suitable expression system to obtain polypeptide with serine-threonine kinase activity. In the case of aurora A, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamH1 5' to the aurora A coding sequence. This allowed the insertion of the aurora A gene in frame with the 6 histidine residues, spacer region and rTEV protease cleavage site encoded by the pFastBac HTc vector. The 3' PCR primer replaced the aurora A stop codon with additional coding sequence followed by a stop codon and a recognition sequence for the restriction endonuclease Not1. This additional coding sequence (5' TAC CCA TAC GAT GTT CCA GAT TAC GCT TCT TAA 3') (SEQ ID NO: 1) encoded for the polypeptide sequence YPYDVPDYAS (SEQ ID NO: 2). This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged Aurora-A protein. Details of the methods for the assembly of recombinant DNA molecules can be found in standard texts, for example Sambrook et al. 1989, Molecular Cloning—A Laboratory Manual, $2^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the aurora A gene was transformed into *E. coli* DH10Bac cells containing the baculovirus genome (bacmid DNA) and via a transposition event in the cells, a region of the pFastBac vector containing gentamycin resistance gene and the aurora A gene including the baculovirus polyhedrin promoter was transposed directly into the bacmid DNA. By selection on gentamycin, kanamycin, tetracycline and X-gal, resultant white colonies should contain recombinant bacmid DNA encoding aurora A. Bacmid DNA was extracted from a small scale culture of several BH10Bac white colonies and transfected into *Spodoptera frugiperda* Sf21 cells grown in TC100 medium (GibcoBRL) containing 10% serum using CellFECTIN reagent (GibcoBRL) following manufacturer's instructions. Virus particles were harvested by collecting cell culture medium 72 hours post transfection. 0.5 ml of medium was used to infect 100 ml suspension culture of Sf21s containing $1 \times 10^7$ cells/ml. Cell culture medium was harvested 48 hours post infection and virus titre determined using a standard plaque assay procedure. Virus stocks were used to infect Sf9 and "High 5" cells at a multiplicity of infection (MOI) of 3 to ascertain expression of recombinant aurora A protein.

For the large scale expression of aurora A kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2 \times 10^6$ cells ml$^{-1}$ they were infected with plaque-pure aurora A recombinant virus at a multiplicity of infection of 1 and harvested 48 hours later. All subsequent purification steps were performed at 4° C. Frozen insect cell pellets containing a total of $2.0 \times 10^8$ cells were thawed and diluted with lysis buffer (25 mM HEPES (N-[2-hydroxyethyl]piperazine-N'-[2-ethanesulphonic acid]) pH7.4 at 4° C., 100 mM KCl, 25 mM NaF, 1 mM Na$_3$VO$_4$, 1 mM PMSF (phenylmethylsulphonyl fluoride), 2 mM 2-mercaptoethanol, 2 mM imidazole, 1 µg/ml aprotinin, 1 µg/ml pepstatin, 1 µg/ml leupeptin), using 1.0 ml per $3 \times 10^7$ cells. Lysis was achieved using a dounce homogeniser, following which the lysate was centrifuged at 41,000 g for 35 minutes. Aspirated supernatant was pumped onto a 5 mm diameter chromatography column containing 500 µl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH7.4 at 4° C., 100 mM KCl, 20 mM imidazole, 2 mM 2-mercaptoethanol). Bound aurora A protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in UV absorbance was collected. The elution fraction, containing active aurora A kinase, was dialysed exhaustively against dialysis buffer (25 mM HEPES pH7.4 at 4° C., 45% glycerol (v/v), 100 mM KCl, 0.25% Nonidet P40 (v/v), 1 mM dithiothreitol).

Each new batch of aurora A enzyme was titrated in the assay by dilution with enzyme diluent (25 mM Tris-HCl pH7.5, 12.5 mM KCl, 0.6 mM DTT). For a typical batch (which may be obtained from Upstate), stock enzyme is diluted 1 µl per ml with enzyme diluent and 20 µl of dilute enzyme is used for each assay well. Test compounds (at 10 mM in dimethylsulphoxide (DMSO) were diluted with water and 10 µl of diluted compound was transferred to wells in the assay plates. "Total" and "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25mM Tris-HOl, 12.7 mM KCl, 2.5 mM NaF, 0.6 mM dithiothreitol, 6.25 mM $MnCl_2$, 7.5 mM ATP, 6.25 µM peptide substrate [biotin-LRRWSLGLRRWSLGLRRWSLGL-RRWSLG]) (SEQ ID NO: 3) containing 0.2 µCi [$\gamma^{33}$P]ATP (Amersham Pharmacia, specific activity $\geq$2500 Ci/mmol) was then added to all test wells to start the reaction. The plates were incubated at room temperature for 60 minutes. To stop the reaction 100 µl 20% v/v orthophosphoric acid was added to all wells. The peptide substrate was captured on positively-charged nitrocellulose P30 filtermat (Whatman) using a 96-well plate harvester (TomTek) and then assayed for incorporation of $^{33}$P with a Beta plate counter. "Blank" (no enzyme) and "total" (no compound) control values were used to determine the dilution range of test compound which gave 50% inhibition of enzyme activity (IC50 values).

(b) In Vitro Aurora B Kinase Inhibition Test

This assay determines the ability of a test compound to inhibit serine-threonine kinase activity. DNA encoding aurora B may be obtained by total gene synthesis or by cloning. This DNA may then be expressed in a suitable expression system to obtain polypeptide with serine-threonine kinase activity. In the case of aurora B, the coding sequence was isolated from cDNA by polymerase chain reaction (PCR) and cloned into the pFastBac system in a manner similar to that described above for aurora A (i.e. to direct expression of a 6-histidine tagged aurora B protein).

For the large scale expression of aurora B kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2 \times 10^6$ cells $ml^{-1}$ they were infected with plaque-pure aurora B recombinant virus at a multiplicity of infection of 1 and harvested 48 hours later. All subsequent purification steps were performed at 4° C. Frozen insect cell pellets containing a total of $2.0 \times 10^8$ cells were thawed and diluted with lysis buffer (50 mM HEPES (N-[2-hydroxyethyl]piperazine-N'-[2-ethanesulphonic acid]) pH7.5 at 4° C., 1 mM $Na_3VO_4$, 1 mM PMSF (phenylmethylsulphonyl fluoride), 1 mM dithiothreitol, 1 µg/ml aprotinin, 1 µg/ml pepstatin, 1 µg/ml leupeptin), using 1.0 ml per $2 \times 10^7$ cells. Lysis was achieved using a sonication homogeniser, following which the lysate was centrifuged at 41,000 g for 35 minutes. Aspirated supernatant was pumped onto a 5 mm diameter chromatography column containing 1.0 ml CM sepharose Fast Flow (Amersham Pharmacia Biotech) which had been equilibrated in lysis buffer. A baseline level of UV absorbance for the eluent was reached after washing the column with 12 ml of lysis buffer followed by 7 ml of wash buffer (50 mM HEPES pH7.4 at 4° C., 1 mM dithiothreitol). Bound aurora B protein was eluted from the column using a gradient of elution buffer (50 mM HEPES pH7.4 at 4° C., 0.6 M NaCl, 1 mM dithiothreitol, running from 0% elution buffer to 100% elution buffer over 15 minutes at a flowrate of 0.5 ml/min). Elution fractions (1.0 ml) corresponding to the peak in UV absorbance was collected. Elution fractions were dialysed exhaustively against dialysis buffer (25 mM HEPES pH7.4 at 4° C., 45% glycerol (v/v), 100 mM KCl, 0.05% (v/v) IGEPAL CA630 (Sigma Aldrich), 1 mM dithiothreitol). Dialysed fractions were assayed for aurora B kinase activity.

Aurora B-INCENP enzyme (as supplied by Upstate) was prepared by activating aurora B (5 µM) in 50 mM Tris-HCl pH 7.5, 0.1 mM EGTA, 0.1% 2-mercaptoethanol, 0.1 mM sodium vandate, 10 mM magnesium acetate, 0.1 mM ATP with 0.1 mg/ml GST-INCENP [826-919] at 30° C. for 30 minutes.

Each new batch of aurora B-INCENP enzyme was titrated in the assay by dilution with enzyme diluent (25 mM Tris-HCl pH7.5, 12.5 mM KCl, 0.6 mM DTT). For a typical batch, stock enzyme is diluted 15 µl per ml with enzyme diluent and 20 µl of dilute enzyme is used for each assay well. Test compounds (at 10 mM in dimethylsulphoxide (DMSO) were diluted with water and 110l of diluted compound was transferred to wells in the assay plates. "Total" and "blank" control wells contained 2.5% DMSO instead of compound. Twenty microlitres of freshly diluted enzyme was added to all wells, apart from "blank" wells. Twenty microlitres of enzyme diluent was added to "blank" wells. Twenty microlitres of reaction mix (25 mM Tris-HCl, 12.7 mM KCl, 2.5 mM NaF, 0.6 mM dithiothreitol, 6.25 mM $MnCl_2$, 15 mM ATP, 6.25 M peptide substrate [biotin-LRRWSLGLRRWSLGLRRWS-LGLRRWSLG]) containing 0.2 µCi [$\gamma^{33}$P]ATP (Amersham Pharmacia, specific activity $\geq$2500 Ci/mmol) was then added to all test wells to start the reaction. The plates were incubated at room temperature for 60 minutes. To stop the reaction 100 µl 20% v/v orthophosphoric acid was added to all wells. The peptide substrate was captured on positively-charged nitrocellulose P30 filtermat (Whatman) using a 96-well plate harvester (TomTek) & then assayed for incorporation of $^{33}$P with a Beta plate counter. "Blank" (no enzyme) and "total" (no compound) control values were used to determine the dilution range of test compound which gave 50% inhibition of enzyme activity (IC50 values).

(c) In vitro Cell Phenotype and Substrate Phosphorylation Assay

This assay is used to determine the cellular effects of compounds on SW620 human colon tumour cells in vitro. Compounds typically cause inhibition of levels of phosphohistone H3 and an increase in the nuclear area of the cells.

$10^4$ SW620 cells per well were plated in 100 µl DMEM media (containing 10% FCS and 1% glutamine) (DMEM is Dulbecco's Modified Eagle's Medium (Sigma D6546)) in costar 96 well plates and left overnight at 37° C. and 5% $CO_2$ to adhere. The cells were then dosed with compound diluted in media (50 µl is added to each well to give 0.00015µ-1 µM concentrations of compound) and after 24 hours of treatment with compound, the cells were fixed.

The cells were first examined using a light microscope and any cellular changes in morphology were noted. 100 µl of 3.7% formaldehyde was then added to each well, and the plate was left for at least 30 minutes at room temperature. Decanting and tapping the plate on a paper towel removed the fixative and plates were then washed once in PBS (Dulbecco's Phosphate Buffered Saline (Sigma D8537)) using an automated plate washer. 100 µl PBS and 0.5% triton X-100 was added and the plates were put on a shaker for 5 minutes. The plates were washed in 100 µl PBS and solution tipped off. 50

μl of primary antibody, 1:500 rabbit anti-phosphohistone H3 in PBS 1% BSA (bovine serum albumin) and 0.5% tween, was added. Anti-phosphohistone H3 rabbit polyclonal 06-750 was purchased from Upstate Biotechnology. The plates were left 1 hour at room temperature on a shaker.

The next day, the antibody was tipped off and the plates were washed twice with PBS. In an unlit area, 50 μl of secondary antibody, 1:10,000 Hoechst and 1:200 Alexa Fluor 488 goat anti rabbit IgGA (cat no. 11008 molecular probes) in PBS 1% BSA, 0.5% tween was added. The plates were wrapped in tin foil and shaken for 1 hour at room temperature. The antibody was tipped off and plates were washed twice with PBS. 200 μl PBS was added to each well, and the plates were shaken for 10 minutes, PBS was removed. 100 μl PBS was added to each well and the plates were sealed ready to analyses Analysis was carried out using an Arrayscan Target Activation algorithm to measure cellular levels of phosphohistone H3 and changes in nuclear area. Results were reported as the effective concentration required to give 50% inhibition of phosphohistone H3 levels and similarly for a 50% increase in nuclear area of cells (EC50 values).

The invention is illustrated herein by means of non-limiting Examples, data and Figures in which, unless otherwise stated:—

(i) yields are given for illustration only and are not necessarily the maximum attainable;

(ii) where product is used for seeding it can be obtained by prior known process such as those described in WO 2004/058781;

(iii) the identity of AZD1152 maleate co-crystal prepared as described herein was confirmed by $^1$H NMR at 400 MHz in hexadeuterated dimethylsulphoxide with added tetramethylsilane (TMS) for reference (TMS=0.00 ppm).

As described herein AZD1152 and AZD1152 HQPA are disclosed in WO 2004/058781. The process details provided in WO2004/058781 in relation to AZD1152, AZD1152 HQPA and all the intermediates en route to said compounds are incorporated herein by reference in their entirety.

PREPARATION METHOD 1

Step 1-Preparation of 7-(3-hydroxypropoxy)quinazolin-4(3H)-one

2-Amino-4-fluorobenzoic acid and 1,3-propanediol were stirred together and heated to 120° C. Formamidine acetate was added and the mixture stirred for 3.5 hour to yield 7-fluoroquinazoline-4-one. A solution of potassium hydroxide in 1,3-propanediol was then added to the mixture over a period of 2 hours and 50 minutes, which was then cooled 15° C. Following this, the mixture was heated to 125° C. for 5 hour before cooling to 75° C. Dilute hydrochloric acid (about 6% w/w) was gradually added to the reaction mixture until pH 4.5 was achieved. The mixture was cooled to 0° C. over 6 hour and maintained at that temperature for a further hour prior to isolation of the crude product by centrifugation. The crude material was washed with water and dried in vacuo before dissolving in methanol at gentle reflux and partially concentrating under reduced pressure at a temperature of 42° C. This solution was then cooled to 0° C. over a period of 3 hour and the resultant product was isolated by filtration, prior to drying in vacuo. 7-(3-Hydroxypropoxy)quinazolin-4(3H)-one was recovered in a 73% yield.

$^1$H-NMR (DMSO $d_6$): 11.90 (br s, 1H), 8.04 (s, 1H), 8.00 (d, 1H), 7.10 (m, 2H), 4.17 (t, 2H), 3.58 (t, 2H), 1.92 (m, 2H): MS (+ve ESI): 221 (M+H)$^+$

Step 2-Preparation of 4-chloro-7-(3-chloropropoxy)quinazoline 7-(3-Hydroxypropoxy)quinazolin-4(3H)-one, toluene and N,N-diisopropyl-formamide (DIPF) were mixed together and heated to 76° C., before thionyl chloride was added over a period of 1 hour at 76° C. Additional thionyl chloride was then added over a period of 1 hour after which the temperature was maintained at 76° C. for 1 hour. The mixture was refluxed for 11 hours to effect a clear solution which was cooled to 38° C. and subjected to vacuum distillation to remove toluene and thionyl chloride. Toluene was then added and the solution kept at 35° C. whilst it was clarified with a filter aid (celite or harborlite and activated carbon). The resulting solution was partially concentrated before heptane was added and the mixture chilled to 0° C. and stirred for 23 hours. The light brown suspension that formed was isolated by filtration, washed with cold heptane then dried in vacuo at 30° C. to yield 4-chloro-7-(3-chloropropoxy)quinazoline (63.6%)

$^1$H-NMR (DMSO $d_6$): 13.25 (br s, 1H), 8.34 (s, 1H), 8.06 (d, 1H), 7.17 (m, 2H), 4.21 (t, 2H), 3.83 (t, 2H), 2.23 (m, 2H): MS (+ve ESI): 257, 259 (M+H)$^+$.

Step 3-Preparation of (3-{[7-(3-chloropropoxy)quinazolin-4-yl]amino}-1H-pyrazol-5-yl)acetic acid 4-Chloro-7-(3-chloropropoxy)quinazoline was added to 1 molar equivalent of a solution of (3-amino-1H-pyrazol-5-yl)acetic acid in N-methylpyrrolidinone (NMP) and then left for a period of 12 hours. Crystallisation of the product was observed to occur with and without seeding and with and without the addition of acetonitrile as an anti-solvent. The resultant solid was isolated by filtration, washed with N-methylpyrrolidinone and acetonitrile and then dried in vacuo to yield (3-{[7-(3-chloropropoxy)quinazolin-4-yl]amino}-1H-pyrazol-5-yl)acetic acid.hydrochloride as an off-white solid:

$^1$H-NMR (DMSO $d_6$; contains NMP as a solvate): 8.92 (s, 1H), 8.8 (d, 1H), 7.46 (pr of d, 1H), 7.38 (d, 1H), 6.7 (s, 1H), 4.32 (t, 2H), 3.85 (t, 2H), 3.73 (s, 2H), 3.3 (t, 2H), 2.7 (s, 3H), 2.51 (m, 6H), 2.27 (m, 2H), 2.18 (t, 2H), 1.93 (m, 2H). MS (+ve ESI): 362.1015 (M+H)$^+$.

Step 4-Preparation of 2-(3-{[7-(3-chloropropoxy)quinazolin-4-yl]amino}-1H-pyrazol-5-yl)-N-(3-fluorophenyl)acetamide 4-Dimethylaminopyridine (DMAP), N-methylmorpholine and 3-fluoroaniline (in a large excess) were added to a suspension of (3-{[7-(3-chloropropoxy)quinazolin-4-yl]amino}-1H-pyrazol-5-yl)acetic acid.hydrochloride in N,N-dimethylacetamide (DMA) and the resulting slurry was stirred at or below room temperature. A solution of 1-ethyl-3-(3-dimethylaminopropyl)carbodiimide hydrochloride (EDCI.HCl) previously dissolved in water was then added in a controlled manner over a period of 8 hour so as to maintain the reaction at ambient temperature. The mixture was seeded with a small amount of product and left to stir for several hours. Anti-solvent acetonitrile followed by water were also added to precipitate more product. The material was isolated by filtration and the cake washed with a mixture of N,N-dimethylacetamide:water:acetonitrile, warm acetonitrile and then dried (in vacuo or under a stream of nitrogen) to yield 2-(3-{[7-(3-chloropropoxy)quinazolin-4-yl]amino}-1H-pyrazol-5-yl)-N-(3-fluorophenyl)acetamide.

$^1$H-NMR (DMSO $d_6$; contains residual DMA): 10.4 (s, 1H), 8.9 (s, 1H), 8.8 (d, 1H), 7.59 (pr of m, 1H), 7.46 (pr of d, 1H), 7.33 (m, 2H), 7.29 (d, 1H), 6.85 (m, 1H), 6.75 (s, 1H), 4.35 (t, 2H), 3.85 (t, 4H), 2.95 (s), 2.83 (s), 2.56 (s), 2.25 (m, 2H), 1.95 (s): MS (+ve ESI): 455 (M+H)$^+$.

Step 5-Preparation of 2-{3-[(7-{3-[ethyl(2-hydroxy-ethyl)amino]propoxy}-quinazolin-4-yl)amino]-1H-pyrazol-5-yl}-N-(3-fluorophenyl)acetamide (AZD1152 HQPA)

2-(3-{[7-(3-Chloropropoxy)quinazolin-4-yl]amino}-1H-pyrazol-5-yl)-N-(3-fluorophenyl)acetamide and 2-(ethylamino)ethanol (12 molar equivalents) were added to N,N-dimethylacetamide under an inert atmosphere (such as provided by nitrogen) and the mixture heated to 90° C. with stirring. After 12 hours, water was added in a controlled manner and the batch seeded with product whilst hot. The mixture was cooled to 20° C. in a carefully controlled manner to crystallise the product in the required form. The product was then filtered and washed with a mixture of water/N,N-dimethylacetamide and acetonitrile. Following this, the cake was slurried for a period with warm acetonitrile (40° C.), filtered, washed with more acetonitrile and then dried (in vacuo or under a stream of nitrogen) to afford the anhydrous 2-{3-[(7-{3-[ethyl(2-hydroxyethyl)amino]propoxy}-quinazolin-4-yl)amino]-1H-pyrazol-5-yl}-N-(3-fluorophenyl)acetamide as an off-white solid in a yield of ~90%.

$^1$H-NMR (DMSO d$_6$): 10.55 (s, 1H), 9.45 (br s, 1H), 8.98 (s, 1H), 8.8 (d, 1H), 7.63 (pr of m, 1H), 7.47 (pr of d, 1H), 7.37 (m, 2H), 7.32 (d, 1H), 6.9 (m, 1H), 6.77 (s, 1H), 4.32 (t, 2H), 3.83 (br s, 2H), 3.76 (t, 2H), 3.35 (m, 2H), 3.25 (m, 4H), 2.25 (m, 2H), 1.25 (t, 3H): MS (+ve ESI): 508.4 (M+H)$^+$.

Step 6-Preparation of mono(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate [AZD1152 t-Bu P(5)ester]

2-{3-[(7-{3-[Ethyl(2-hydroxyethyl)amino]propoxy}-quinazolin-4-yl)amino]-1H-pyrazol-5-yl}-N-(3-fluorophenyl)acetamide and pyridine.hydrochloride were mixed in N,N-dimethylacetamide and the solution chilled to −15° C. Di-tert-butyl diethylphosphoramidite (1.5-2.1 molar equivalents) was then added whilst the temperature was maintained. The reaction mixture was treated in situ with 30% w/w hydrogen peroxide (about 4.2 mole equivalents) whilst the temperature was kept below ambient temperature. Remaining hydrogen peroxide was destroyed by the addition of sodium metabisulphite (as a 10% w/v aqueous solution) whilst maintaining the temperature below 40° C. The resulting solution of di-tert-butyl 2-[[3-({4-[(5-{2-[(3-fluorophenyl)amino]-2-oxoethyl}-1H-pyrazol-3-yl)amino]quinazolin-7-yl}oxy)propyl](ethyl)amino]ethyl phosphate was then heated to 40° C. and sodium hydroxide solution (2M) added to adjust to pH 5-6.5. The temperature and pH was maintained for a period of about 90 minutes with seeding. Water was then charged and the pH adjusted further to within the range pH 8-9 to optimise the recovery. The warm reaction mixture was filtered directly to afford mono-tert-butyl 2-[[3-({4-[(5-{2-[(3-fluorophenyl)amino]-2-oxoethyl}-1H-pyrazol-3-yl)amino]quinazolin-7-yl}oxy)propyl](ethyl)amino]ethyl phosphate which was washed with a mixture of N,N-dimethylacetamide/water and water and finally dried (in vacuo or a stream of a suitable inert gas) to afford mono(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate as an off-white solid at a yield of between 86-93%.

$^1$H-NMR (DMSO d$_6$): 10.48 (s, 1H), 9.75 (br s, 1H), 8.98 (s, 1H), 8.85 (d, 1H), 7.67 (pr of m, 1H), 7.48 (pr of d, 1H), 7.37 (m, 2H), 7.3 (d, 1H), 6.87 (m, 1H), 6.83 (s, 1H), 4.34 (t, 2H), 4.28 (m, 2H), 3.88 (s, 2H), 3.53 (m, 2H), 3.43 (m, 2H), 3.33 (m, 2H), 2.3 (m, 2H), 1.47 (s, 9H), 1.32 (t, 3H): MS (+ve ESI): (M+H)$^+$ 644.2761 fragment (less butyl) 588.2147.

Step 7-Preparation of 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate (AZD1152)

Mono(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate was suspended in a 1:1 mixture of water/tetrahydrofuran (THF) and treated at elevated temperatures (preferably 50-60° C.) with an excess of between 1.5 and 3.0 molar equivalents of hydrochloric acid for a period of about 1 hour. The hot solution was then basified using 2.0M sodium hydroxide to within the range pH 4.5-5.5, cooled to 60° C. and seeded. Water was added to the slurry in a controlled manner with controlled cooling of the crystallisation mixture to room temperature and the product was isolated by filtration. The filter-cake was washed with water and dried in vacuo. After drying, the solid 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate was equilibrated under ambient conditions to constant weight to give a hydrated form as a pale yellow needle-like material.

$^1$H-NMR (DMSO d$_6$): MS(+ve ESI): 587.8 (M+H)$^{+1}$H-NMR (DMSO d$_6$): 10.53 (s, 1H), 8.57 (s, 1H), 8.54 (d, 1H), 7.62 (d, 1H), 7.37 (m, 2H), 7.27 (s, 1H), 7.21 (d, 1H), 6.88 (m, 1H), 6.65 (s, 1H), 4.27 (t, 2H), 4.05 (m, 2H), 3.75 (s, 2H), 3.24 (m, 2H), 3.21 (t, 2H), 3.13 (q, 2H), 2.18 (m, 2H), 1.24 (t, 3H): MS (+ve ESI): 588 (M+H)$^+$. $C_{26}H_{31}FN_7O_6P$+3.0H$_2$O requires C, 48.7%; H, 5.8%; N, 15.3%; Found C, 48.8%; H, 5.35%; N, 15.15%.

Step 8-Preparation of 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate.maleate [AZD1152 maleate]

2-Butenedioic acid (Z) (1.57 molar equivalents; 449.80 µmoles; 52.21 mg) was dissolved in methanol (123.54 mmoles; 5.00 ml; 3.96 g) and to this solution was added a previously prepared methanolic solution of AZD1152 (as the free form trihydrate—1.00 molar equivalents, 286.14 µmoles; 40.00 mL; 31.87 g) followed by more methanol (123.54 mmoles; 5.00 mL; 3.96 g). The mixture was left to stir overnight at room temperature. A white suspension was produced and the solid recovered by filtration then dried in vacuo. Analysis by NMR confirmed the co-crystal was the maleate.

Alternative Step 8:

Crude AZD1152 (estimated at 7.44 g @ 100%, 11.61 millimoles) was added to dimethylsulphoxide (36 ml) and left at ambient to produce a pale brown solution. To this solution was added a solution of maleic acid (1.76 g, 15.16 millimoles, 1.31 mole equivalents) in methanol (36 ml) and the mixture left to stand overnight at ambient temperature. Next day an aliquot of the clear solution was transferred to a vial, scratched and left sealed for several hours. A deposit of white solid formed and this was transferred to the flask and left to stir. Gradually the solution turned turbid and solid deposited. The slurry was left to settle for several days and finally filtered. The cake was washed with a 1:1 mixture of dimethylsulphoxide/methanol (15 ml in total), slurried in situ with methanol (3×25 ml) and then dried in vacuo. NMR confirmed the solid to be the maleate co-crystal of AZD1152 (in about a 78.7% yield).

PREPARATION METHOD 2

Step 1-Preparation of 2-(3-{[7-(3-chloropropoxy) quinazolin-4-yl]amino}-1H-pyrazol-5-yl)-N-(3-fluorophenyl)acetamide To a suspension of (3-{[7-(3-chloropropoxy)quinazolin-4-yl]amino}-1H-pyrazol-5-yl)acetic acid.hydrochloride (prepared as described in Preparation Method 1 above) in N,N-dimethylacetamide (DMA) is added 4-dimethylaminopyridine (DMAP) whilst maintaining a temperature of 15-25° C. (ideally 15° C.) followed by N-methylmorpholine whilst also maintaining the temperature. 3-Fluoroaniline (in a large excess which ideally is between 10-15 mole equivalents) is added at such a rate as to maintain the temperature below 25° C. Meanwhile 1-ethyl-3-(3-dimethylaminopropyl)carbodiimide hydrochloride (EDCI.HCl) is dissolved in water to afford a solution about 42% w/v (the quantity of water present is important to the outcome of the crystallisation later in the process). This solution is added in a controlled manner to the slurry over a period of 8 hour so as to maintain the reaction between 20-25° C.; then the mixture is seeded with crystals of the preferred form of the product (ideally an amount of about 1% of the expected yield). The mixture is stirred for about 16 hours whilst maintaining the temperature (ideally 20-25° C.) then anti-solvents acetonitrile followed by water are added in a controlled manner and to maintain the temperature between 20-25° C. followed by an extended stir of about 21 hours; this is to optimise the recovery and form of the product. The material is isolated by filtration and the cake washed with a mixture of N,N-dimethylacetamide:water:acetonitrile (volume ratios of 5:3:2), acetonitrile and then dried (in vacuo or under a stream of nitrogen) to afford 2-(3-{[7-(3-chloropropoxy)quinazolin-4-yl]amino}-1H-pyrazol-5-yl)-N-(3-fluorophenyl)acetamide containing some DMA in about 76-78% yield.

$^1$H-NMR (DMSO d$_6$; contains residual DMA): 10.4 (s, 1H), 8.9 (s, 1H), 8.8 (d, 1H), 7.59 (pr of m, 1H), 7.46 (pr of d, 1H), 7.33 (m, 2H), 7.29 (d, 1H), 6.85 (m, 1H), 6.75 (s, 1H), 4.35 (t, 2H), 3.85 (t, 4H), 2.95 (s), 2.83 (s), 2.56 (s), 2.25 (m, 2H), 1.95 (s): MS (+ve ESI): 455 (M+H)$^+$.

Step 2-(Preparation of 2-{3-[(7-{3-[ethyl(2-hydroxyethyl)amino]propoxy}-quinazolin-4-yl)amino]-1H-pyrazol-5-yl}-N-(3-fluorophenyl)acetamide (AZD1152 HQPA)

2-(3-{[7-(3-Chloropropoxy)quinazolin-4-yl]amino}-1H-pyrazol-5-yl)-N-(3-fluorophenyl)acetamide and 2-(ethylamino)ethanol (ideally 12 molar equivalents) were added to N,N-dimethylacetamide under an inert atmosphere (such as provided by nitrogen) and the mixture heated to 90° C. with stirring. After a period of 12-16 hours (ideally 12 hours) the reaction is cooled back to about 85° C. and water added in a controlled manner to maintain the temperature between 80-85° C. The batch is adjusted to 80° C. and seeded with crystals of the preferred form of the product (ideally an amount of about 1% of the expected yield). The mixture was cooled to 20° C. in a carefully controlled manner over a period of about 20 hours so as to crystallise the product in the required form and of a size sufficient to afford a good filtration rate. The product is then filtered and washed with a mixture of water/N,N-dimethylacetamide and acetonitrile and suitably deliquored to afford a hydrated form of the product. Following this, the cake is slurried in situ for a period (ideally 2 hours) with warm acetonitrile (ideally at a temperature of 40° C.) then filtered, washed with more acetonitrile and then dried (in vacuo or under a stream of nitrogen) to afford the almost anhydrous 2-{3-[(7-{3-[ethyl(2-hydroxyethyl)amino]propoxy}-quinazolin-4-yl)amino]-1H-pyrazol-5-yl}-N-(3-fluorophenyl)acetamide as an off-white solid in a yield of 85-90%.

$^1$H-NMR (DMSO d$_6$): 10.55 (s, 1H), 9.45 (br s, 1H), 8.98 (s, 1H), 8.8 (d, 1H), 7.63 (pr of m, 1H), 7.47 (pr of d, 1H), 7.37 (m, 2H), 7.32 (d, 1H), 6.9 (m, 1H), 6.77 (s, 1H), 4.32 (t, 2H), 3.83 (br s, 2H), 3.76 (t, 2H), 3.35 (m, 2H), 3.25 (m, 4H), 2.25 (m, 2H), 1.25 (t, 3H): MS (+ve ESI): 508.4 (M+H)$^+$.

Step 3-Preparation of mono(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl) amino]ethyl phosphate [AZD1152 t-Bu P(5)ester]

To a slurry of pyridine.hydrochloride in N,N-dimethylacetamide was charged a solution of 2-{3-[(7-{3-[Ethyl(2-hydroxyethyl)amino]propoxy}-quinazolin-4-yl)amino]-1H-pyrazol-5-yl}-N-(3-fluorophenyl)acetamide and di-tert-butyl diethylphosphoramidite (ideally 1 molar equivalents) in N,N-dimethylacetamide over an extended period (ideally 3 hours) and maintaining the temperature between −20 to −10° C. (ideally −15° C.). This is followed by the further addition of di-tert-butyl diethylphosphoramidite (ideally 0.5 molar equivalents) during a period of 1 hour also maintaining the temperature between −20 to −10° C. (ideally −15° C.).

The reaction mixture is treated in situ with 30% w/w hydrogen peroxide (about 4.2 mole equivalents) whilst the temperature was kept below −10° C. (ideally −12 to −8° C.) and held for a period at this temperature (ideally 16 hours). Remaining hydrogen peroxide is destroyed by the addition of sodium metabisulphite (as a 10% w/v aqueous solution) whilst maintaining the temperature below 40° C.

The resulting solution of di-tert-butyl 2-[[3-({4-[(5-{2-[(3-fluorophenyl)amino]-2-oxoethyl}-1H-pyrazol-3-yl)amino] quinazolin-7-yl}oxy)propyl](ethyl)amino]ethyl phosphate was then heated to 40° C. and sodium hydroxide solution (ideally 2M) added to adjust to pH 5.5-6.5 (ideally pH 6) with seeding with suitably crystalline material. The temperature is held and a range of pH 5-6 maintained by the addition of extra sodium hydroxide solution for a period of at least 2 hours. Water is then charged and the pH adjusted further to within the range pH 8-9 (ideally pH 8.8) whilst maintaining the temperature (ideally 40° C. but within range 35-45° C.) for a period of 16 hours so as to optimise the recovery. The warm reaction mixture is filtered directly to afford mono-tert-butyl 2-[[3-({4-[(5-{2-[(3-fluorophenyl)amino]-2-oxoethyl}-1H-pyrazol-3-yl)amino]quinazolin-7-yl}oxy)propyl](ethyl) amino]ethyl phosphate which was washed several times with water and finally dried (either in vacuo or a stream of a suitable inert gas) to afford the mono(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate as an off-white solid at a yield of between 86-93%.

$^1$H-NMR (DMSO d$_6$): 10.48 (s, 1H), 9.75 (br s, 1H), 8.98 (s, 1H), 8.85 (d, 1H), 7.67 (pr of m, 1H), 7.48 (pr of d, 1H), 7.37 (m, 2H), 7.3 (d, 1H), 6.87 (m, 1H), 6.83 (s, 1H), 4.34 (t,

2H), 4.28 (m, 2H), 3.88 (s, 2H), 3.53 (m, 2H), 3.43 (m, 2H), 3.33 (m, 2H), 2.3 (m, 2H), 1.47 (s, 9H), 1.32 (t, 3H): MS (+ve ESI): (M+H)+ 644.2761 fragment (less butyl) 588.2147.

Step 4-Preparation of 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate (AZD1152)

Mono(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate was suspended in a mixture of water/tetrahydrofuran (THF) and treated with an excess of between 1.5 and 3.0 molar equivalents of hydrochloric acid (ideally of a concentration of 2M and containing 1.5 mole equivalents). The mixture is heated to 55-65° C. (ideally 60° C.) and held at 60° C. for about 1 hour. The hot solution is then basified using sodium hydroxide (preferably of 2M concentration and containing 1.7 mole equivalents) to afford a pH within the range pH 5.0-5.5 and then seeded at 55-65° C. (ideally 60° C.) with crystals of the preferred form of the product (ideally an amount of about 0.05% w/w of the expected yield). The mixture is stirred at this temperature for at least one hour before water is added and the slurry stirred and cooled in a controlled manner over a period of about 12 hours prior to stirring at ambient temperature for at least 4 hours and then isolating the product by filtration. The filtercake is washed successively with water then THF and dried either in vacuo or using a humidification procedure whereby an inert gas dampened with water vapour is passed over the solid until a constant weight is obtained. After the drying in vacuo the solid 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate is equilibrated under ambient conditions to constant weight to give a hydrated form as a pale yellow needle-like material. The product is obtained in about 81% yield.

$^1$H-NMR (DMSO d$_6$): MS (+ve ESI): 587.8 (M+H)$^{+1}$H-NMR (DMSO d$_6$): 10.53 (s, 1H), 8.57 (s, 1H), 8.54 (d, 1H), 7.62 (d, 1H), 7.37 (m, 2H), 7.27 (s, 1H), 7.21 (d, 1H), 6.88 (m, 1H), 6.65 (s, 1H), 4.27 (t, 2H), 4.05 (m, 2H), 3.75 (s, 2H), 3.24 (m, 2H), 3.21 (t, 2H), 3.13 (q, 2H), 2.18 (m, 2H), 1.24 (t, 3H): MS (+ve ESI): 588 (M+H)$^+$. $C_{26}H_{31}FN_7O_6P+3.0H_2O$ requires C, 48.7%; H, 5.8%; N, 15.3%; Found C, 48.8%; H, 5.35%; N, 15.15%.

Step 5-Preparation of 2-{ethyl[3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate.maleate [AZD1152 maleate]

2-Butenedioic acid (Z) (1.57 molar equivalents; 449.80 μmoles; 52.21 mg) was dissolved in methanol (123.54 mmoles; 5.00 ml; 3.96 g) and to this solution was added a previously prepared methanolic solution of AZD1152 (as the free form trihydrate—1.00 molar equivalents, 286.14 μmoles; 40.00 mL; 31.87 g) followed by more methanol (123.54 mmoles; 5.00 mL; 3.96 g). The mixture was left to stir overnight at room temperature. A white suspension was produced and the solid recovered by filtration then dried in vacuo. Analysis by NMR confirmed the co-crystal was the maleate of AZD1152.

Alternative to Step 5 Above:

Crude AZD1152 (estimated at 7.44 g @100%, 11.61 millimoles) was added to dimethylsulphoxide (36 ml) and left at ambient to produce a pale brown solution. To this solution was added a solution of maleic acid (1.76 g, 15.16 millimoles, 1.31 mole equivalents) in methanol (36 ml) and the mixture left to stand overnight at ambient temperature. Next day an aliquot of the clear solution was transferred to a vial, scratched and left sealed for several hours. A deposit of white solid formed and this was transferred to the flask and left to stir. Gradually the solution turned turbid and solid deposited. The slurry was left to settle for several days and finally filtered. The cake was washed with a 1:1 mixture of dimethylsulphoxide/methanol (15 ml in total), slurried in situ with methanol (3×25 ml) and then dried in vacuo. Analysis by NMR confirmed the co-crystal was the maleate of AZD1152 (in about a 78.7% yield).

Further Alternative to Step 5 Above:

AZD1152 (as the free form trihydrate—1.00 molar equivalent, 8.51 mmoles; 5.74 g) and 2-butenedioic acid (Z) (1.20 molar equivalents; 10.2 mmoles; 1.19 g) are dissolved in dimethylsulphoxide (35 ml) and heated to 60° C. The anti-solvent acetonitrile (20 ml) was added to the hot mixture then the mixture is seeded with crystals of the preferred form of the product AZD1152 Maleate (0.005 molar equivalents; 42.6 micromoles; 30.7 mg—ideally an amount of about 0.5% w/w of the expected yield). The reaction mixture is held at 60° C. for 4 hours before a further charge of acetonitrile (40 ml) is added over a period of 3 hours. The mixture is left agitating at 60° C. for 12-20 hours (ideally 16 hours). The reaction is cooled to 20° C. in a controlled manner and the product isolated by filtration. The cake is washed with a mixture of dimethylsulphoxide/acetonitrile (1:2 volume ratio) followed by acetonitrile. The solid is dried in vacuo or under a stream of warm inert gas (ideally 40° C.) to afford the AZD1152 Maleate as a white solid in about 88% yield.

Characterisation Data

Nuclear Magnetic Resonance Spectroscopy

The structure and approximate ratio of components in the co-crystal can be confirmed with proton NMR spectroscopy. Typical data are shown below.

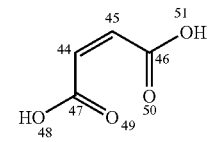

| Atom | Chemical shift/ppm $^1$H |
|---|---|
| 1 | NR |
| 2 | 7.63 (m) |
| 3 | NR |
| 4 | 6.89 (m) |
| 5 | 7.33 (m) |
| 6 | 7.37 (m) |
| 7 | NR |
| 8 | 9.76* (s, broad) |
| 9 | NR |
| 10 | NR |
| 11 | 6.77 (s) |
| 12 | NR |
| 13 | 3.85 (s) |
| 14 | NR |
| 15 | 10.51 (s) |
| 16 | 11.99* (s, broad) |
| 17 | 7.48 (dd, 9.1, 2.4) |
| 18 | NR |
| 19 | 7.29 (d, 2.4) |
| 20 | 8.81 (d, 9.3) |
| 21 | NR |
| 22 | NR |
| 23 | NR |
| 24 | 8.98 (s) |
| 25 | NR |
| 26 | NR |
| 27 | NR |
| 28 | 4.32 (2H t, 5.8) |
| 29 | 2.25 (m) |
| 30 | 3.37 (m) |
| 31 | NR |
| 32 | 3.48 (m) |
| 33 | 4.22 (m) |
| 34 | 3.30 (2H q, 7.1) |
| 35 | 1.28 (3H t, 7.1) |
| 36 | NR |
| 37 | NR |
| 38 | NR |
| 39 | NR |
| 40 | NR |
| 41 | NR |
| 42 | 14.0 (s, broad) |
| 43 | 14.0 (s, broad) |
| 44 | 6.28 (s) |
| 45 | 6.28 (s) |
| 46 | NR |
| 47 | NR |
| 48 | 14.0 (s, broad) |
| 49 | NR |
| 50 | NR |
| 51 | 14.0 (s, broad) |

NR = No Resonance

NMR integration fits approximately with a 1:1.04 maleic acid to AZD1152 ratio.

Differential Scanning Calorimetry

Differential Scanning Calorimetry (DSC) analysis was conducted on AZD1152 maleate co-crystal prepared according to Preparation Methods 1 and 2 using a Mettler DSC820e. Samples of typically less than 5 mg of material contained in a 40 μl aluminium pan fitted with a pierced lid were heated over the temperature range 25° C. to 325° C. at a constant heating rate of 10° C. per minute. A purge gas using nitrogen was used—flow rate 100 ml per minute.

Figure 2:
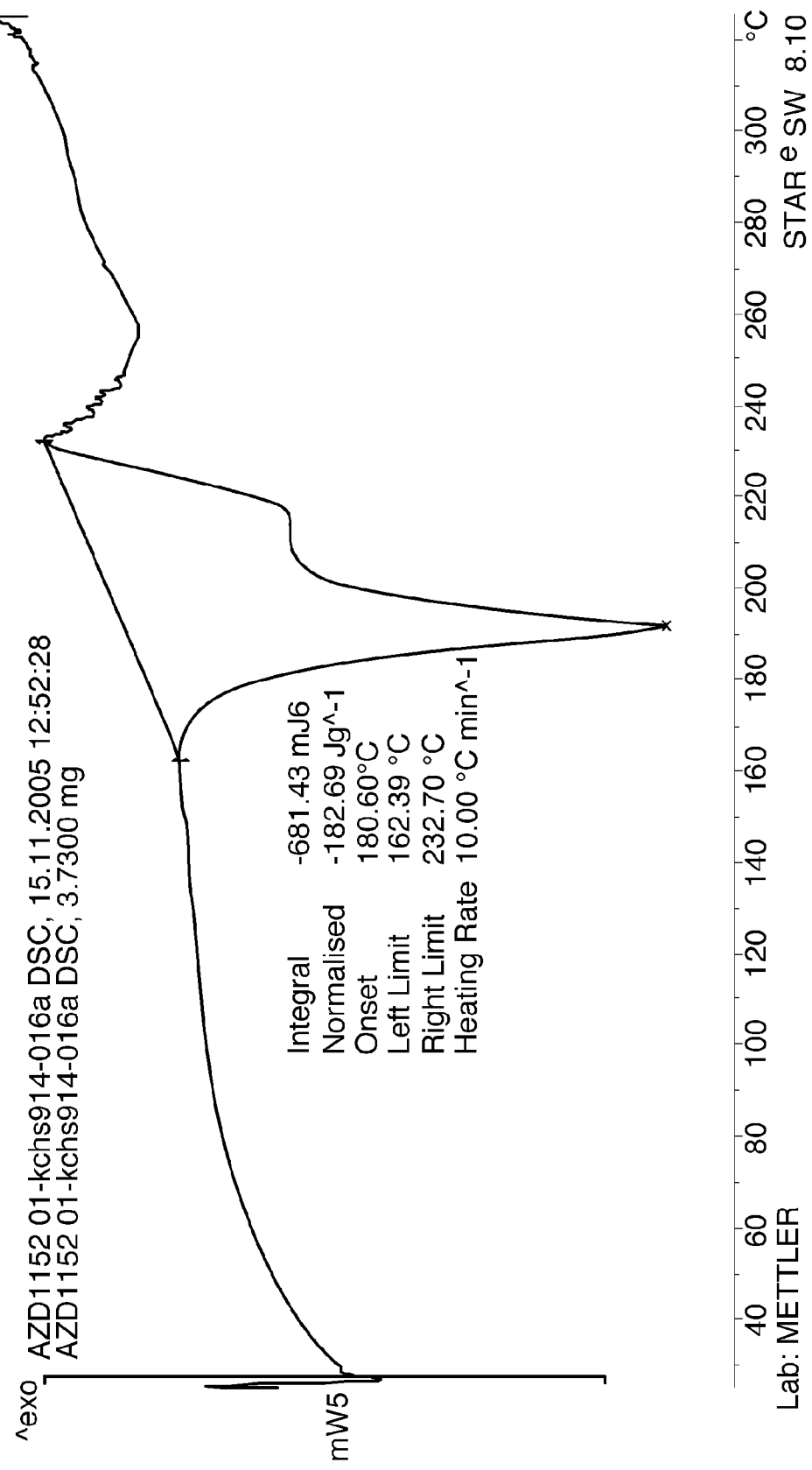
FIG. 2: A Differential Scanning Calorimetry Thermogram for AZD1152 maleate co-crystal prepared according to Method 1 above.

The results for a batch of AZD1152 maleate co-crystal prepared according to Method 1 above (see FIG. 2) indicate that the maleate co-crystal shows a large, sharp endotherm with an onset temperature of 180° C. due to melting. Following the melt a large endothermic event is observed due to the degradation of the maleic acid following the melt. It will be understood that the onset and/or peak temperature values of the DSC may vary slightly from one machine to another, one method to another or from one sample to another, and so the values quoted are not to be construed as absolute.

Figure 3:
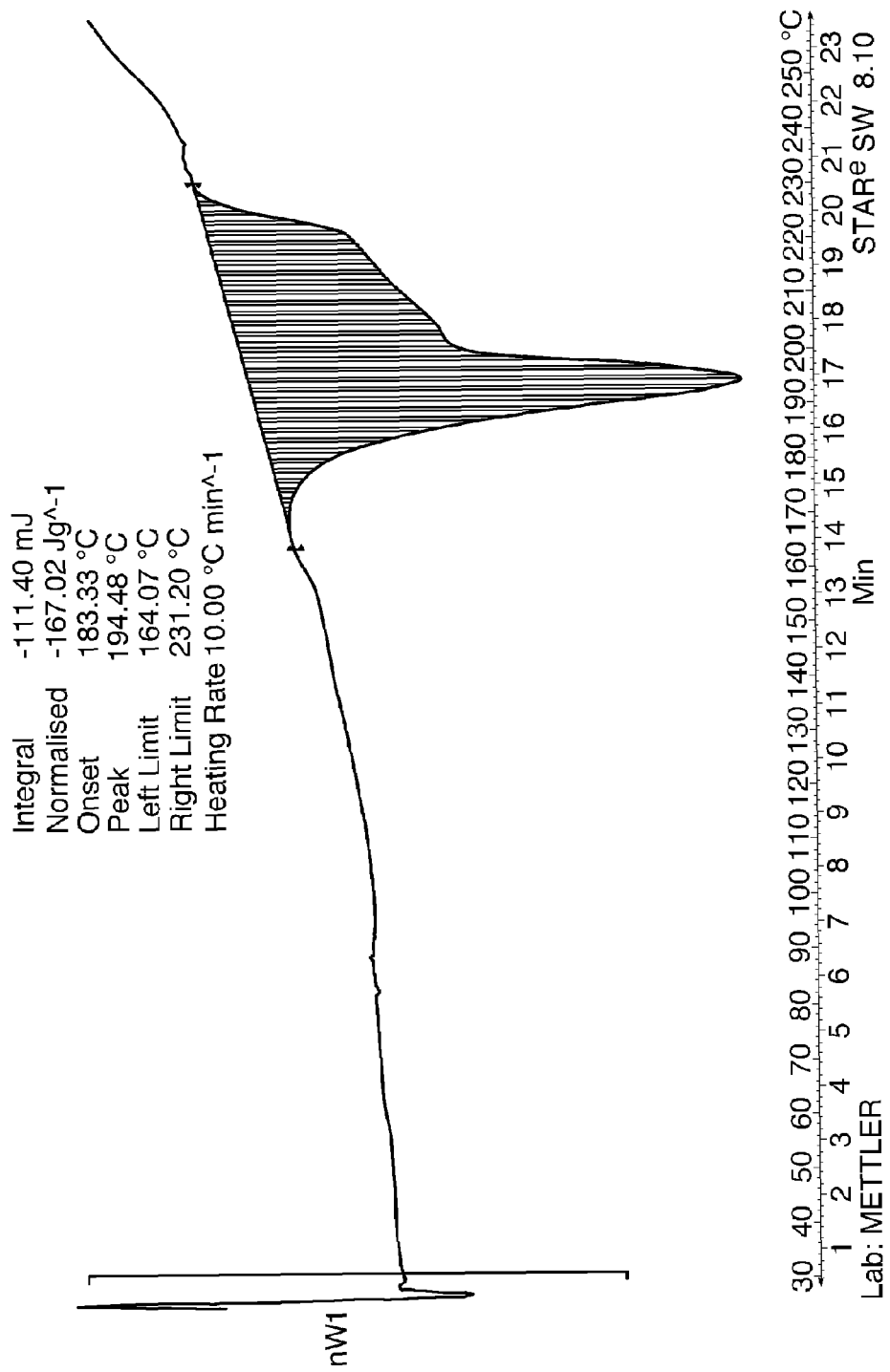
FIG. 3: A Differential Scanning Calorimetry Thermogram for AZD1152 maleate co-crystal prepared according to Method 2 above.

The results for the AZD1152 maleate co-crystal prepared by Method 2 above (see FIG. 3) indicate that the maleate co-crystal shows a large, sharp endotherm with an onset temperature of 183° C. due to melting. Following the melt a large endothermic event is observed due to the degradation of the maleic acid following the melt. It will be understood that the onset and/or peak temperature values of the DSC may vary slightly from one machine to another, one method to another or from one sample to another, and so the values quoted are not to be construed as absolute.

Dynamic Vapour Sorption

Analytical Instrument: Surface Measurements Systems Dynamic Vapour Sorption Analyser.

About 5 mg of material contained in a quartz holder at a specified temperature was subjected to humidified nitrogen at a flow rate of 200 ml/minute of nitrogen at 25° C. at the following relative humidities (RH): 0, 20, 40, 60, 80, 95, 80, 60, 40, 20, 0% RH in duplicate.

The weight of the material at a particular relative humidity was monitored until it was stable according to a weight criteria of 0.002% weight change per minute averaged over 10 minutes. If the weight was still changing then it stayed at a particular relative humidity until the weight was stable (up to a maximum time of 12 hours).

Figure 4:
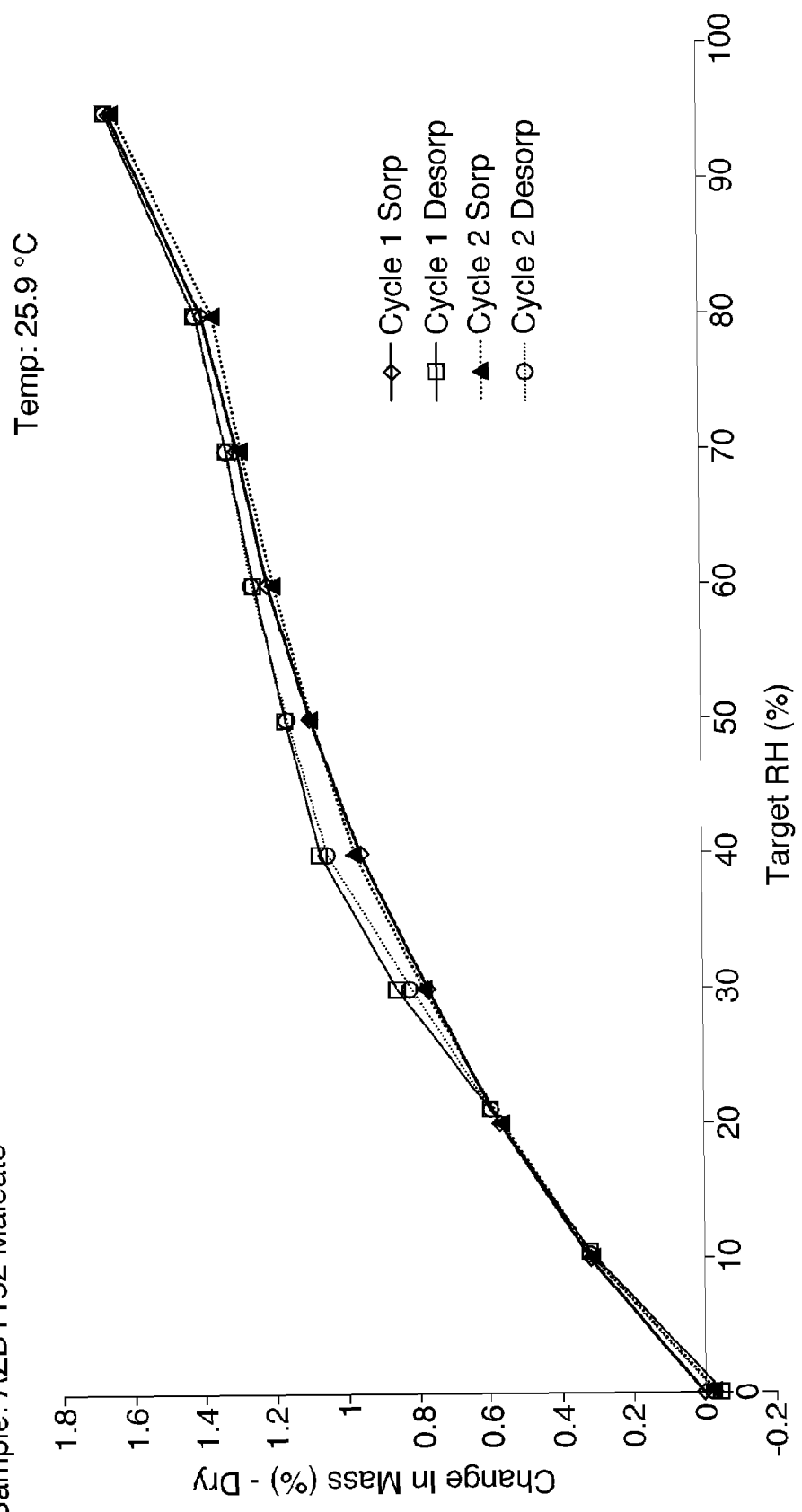
FIG. 4: Dynamic Vapour Sorption Isotherm plot for a batch of AZD1152 maleate co-crystal prepared according to Method 1 above.

The results for a batch of AZD1152 maleate co-crystal prepared according to Method 1 are shown in FIG. 4. The results for a batch of AZD1152 maleate co-crystal prepared according to Method 2 above are shown in FIG. 5.

Figure 5:
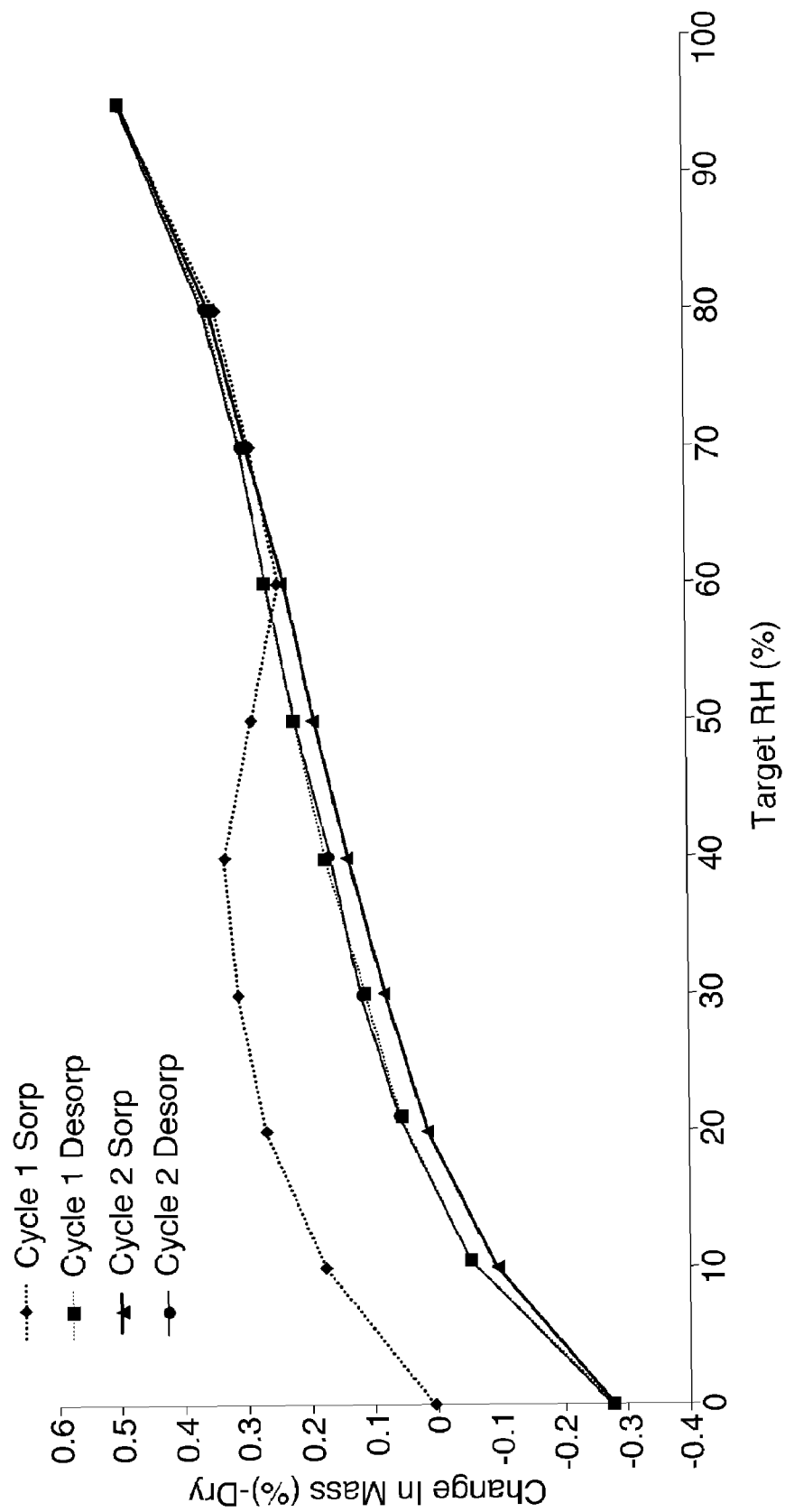
FIG. 5: Dynamic Vapour Sorption Isotherm plot for a batch of AZD1152 maleate co-crystal prepared according to Method 2 above.

The Dynamic Vapour Sorption results shown in FIGS. 4 and 5 indicate that the sample is non-hygroscopic and the weight uptake is attributed to surface adsorption. The weight loss observed in FIG. 5 during Cycle 1 is attributed to a small amount of solvent present in the sample from manufacture. This is confirmed by the reduced weight at 0% RH. Once this solvent has evaporated the material maintains its weight at 0% RH. This observation will be fully understood by the person skilled in the art.

Figure 6:
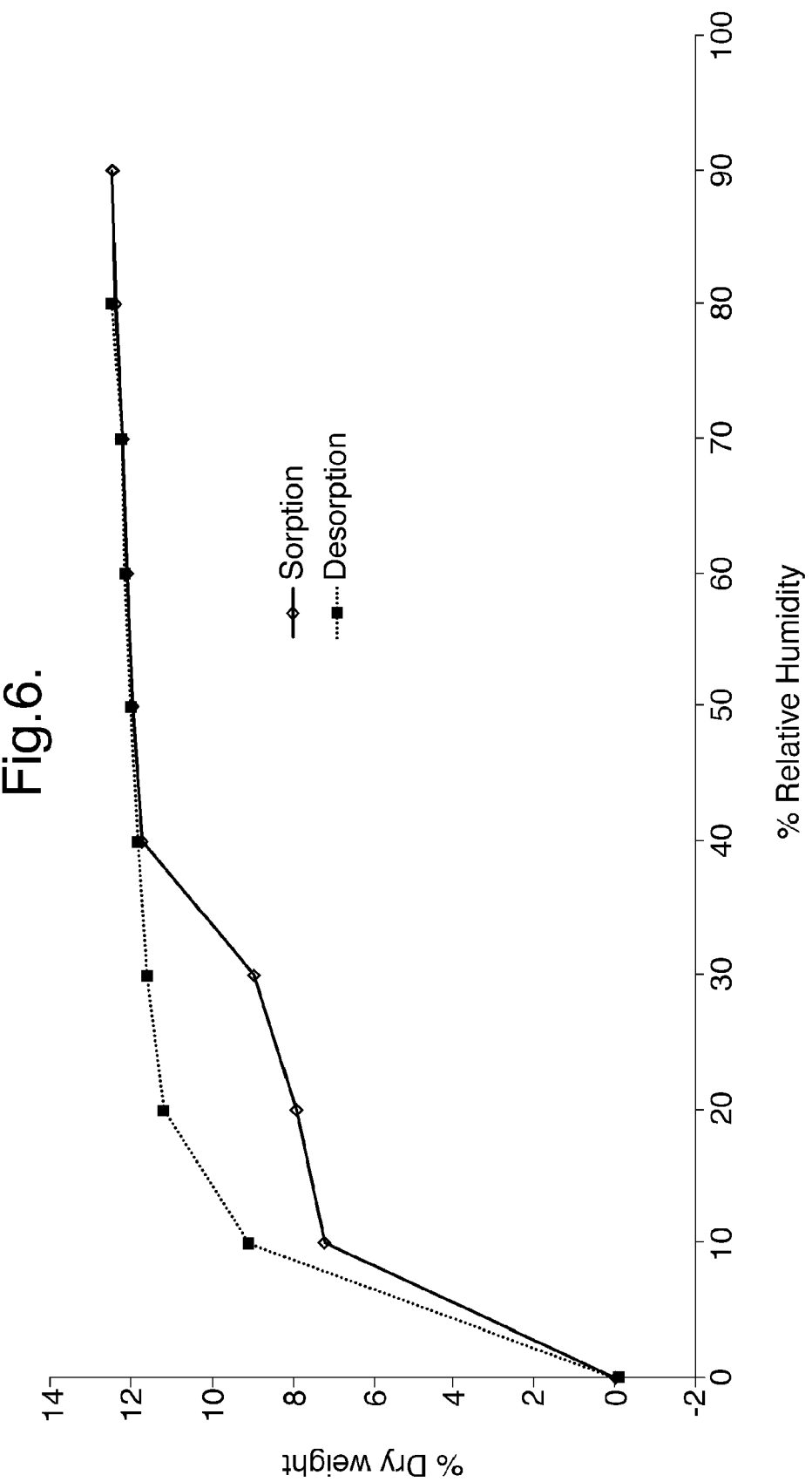
FIG. 6: Dynamic Vapour Sorption Isotherm plot for AZD1152 free form.

The Dynamic Vapour Sorption of AZD1152 free form is shown in FIG. 6.

Dynamic Vapour Sorption of AZD1152 free form indicates that the level of water is quite variable depending on the relative humidity of storage. This change in water level is due to different hydration states which can range from a dehydrated state to a tetrahydrated state and higher.

X-Ray Powder Diffraction

Figure 1:
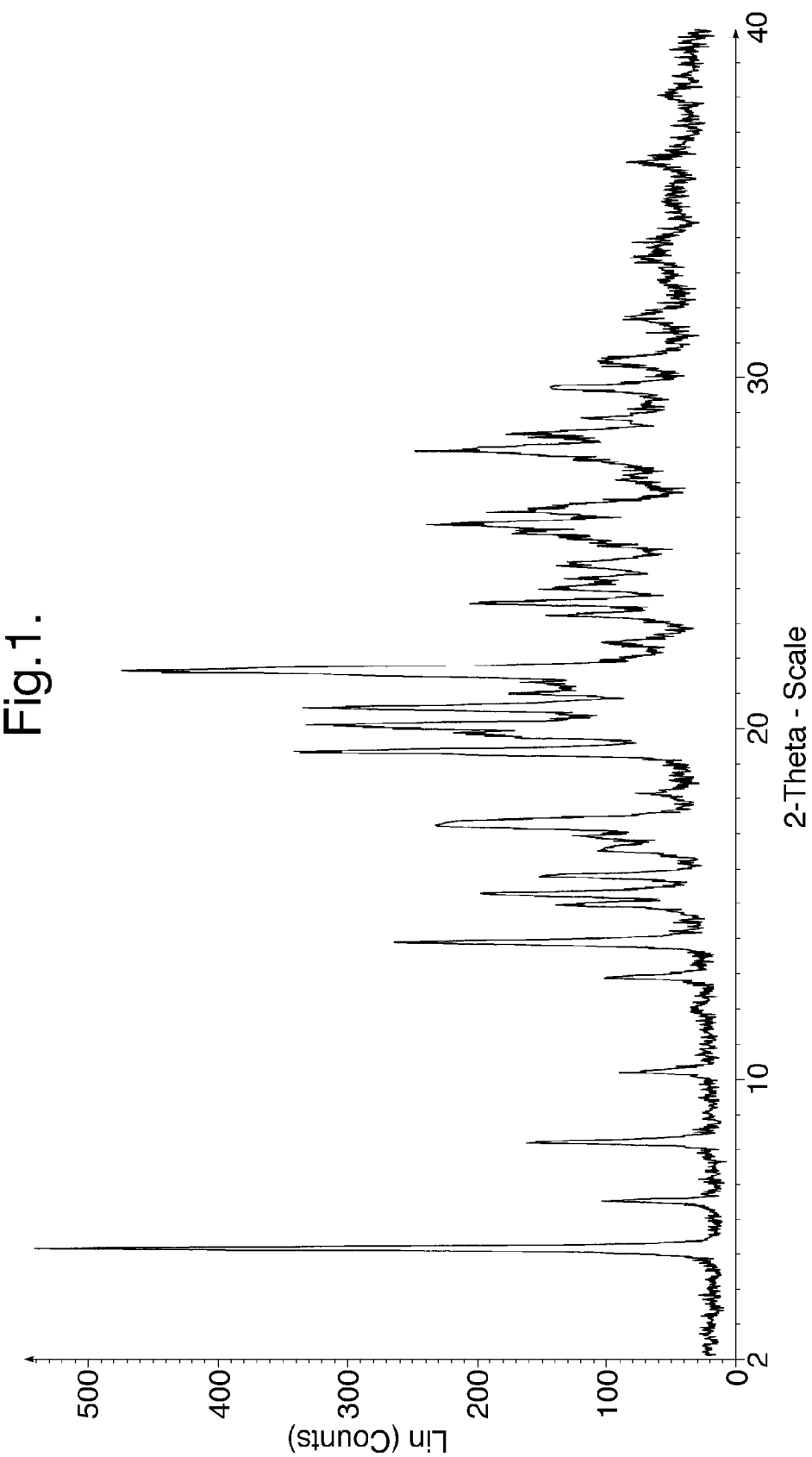
FIG. 1: X-Ray Powder Diffraction Pattern for the maleate co-crystal of AZD1152 (prepared by Method 1 above)—with the 2θ values plotted on the horizontal axis and the relative line intensity (count) plotted on the vertical axis.

It is stated above that the X-ray powder diffraction pattern for the maleate co-crystal of AZD1152 is shown in FIG. 1.

Figure 7:
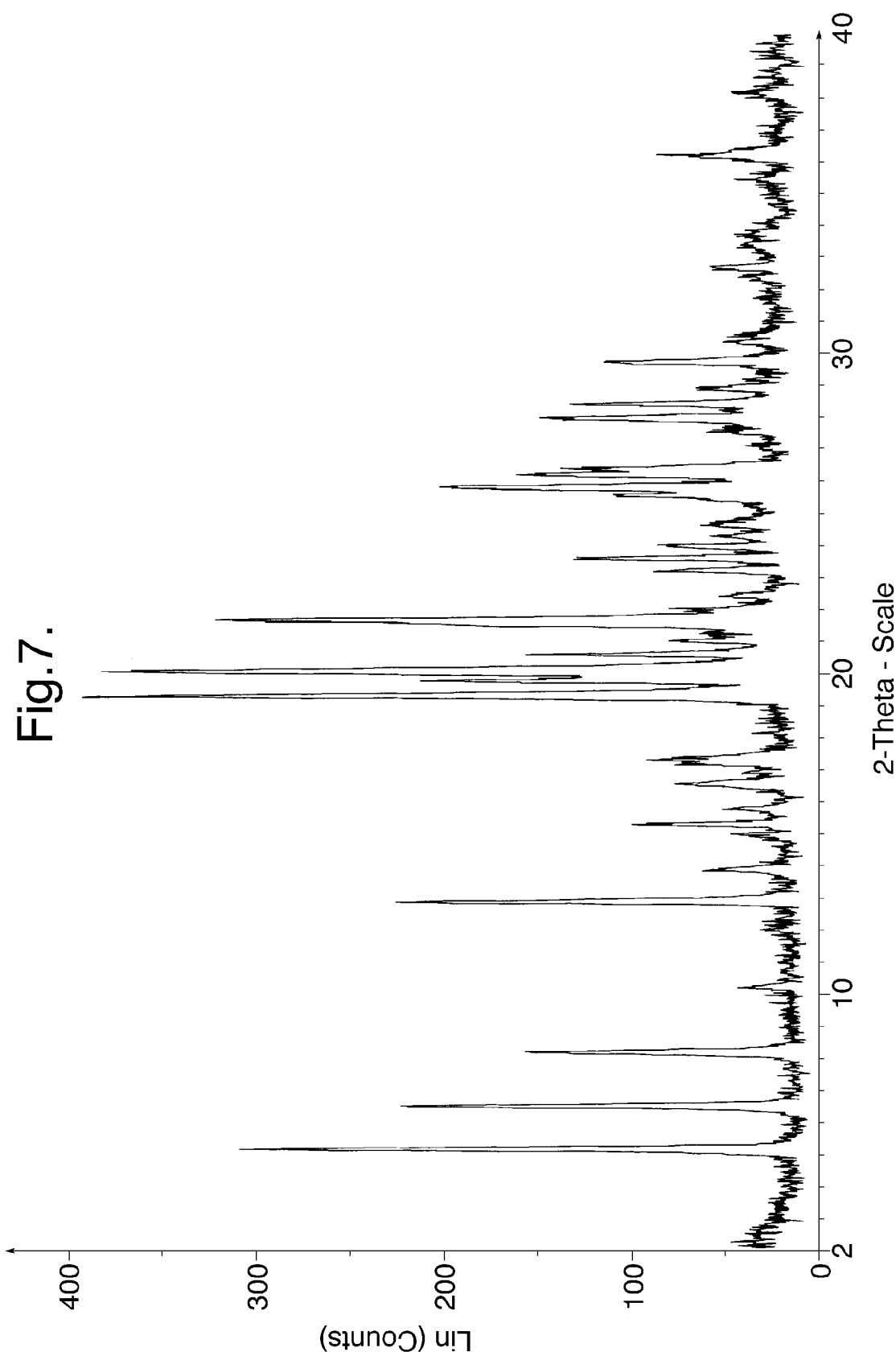
FIG. 7: X-Ray Powder Diffraction Pattern for the maleate co-crystal of AZD1152 (prepared by Method 2 above)—with the 2θ values plotted on the horizontal axis and the relative line intensity (count) plotted on the vertical axis.

A further manufacturing method for AZD1152 maleate has been presented in Method 2 above. The X-ray powder diffraction pattern for the maleate co-crystal of AZD1152 produced by Method 2 is shown in FIG. 7. The key peaks are shown in table 2 below.

TABLE 2

| Angle (2-theta) | Relative intensity (%) |
| --- | --- |
| 5.13 | 80.3 |
| 6.45 | 57.9 |
| 8.14 | 40.5 |
| 10.18 | 9.1 |
| 11.96 | 7.8 |
| 12.85 | 58.4 |
| 13.85 | 14.3 |
| 14.96 | 12.5 |
| 15.27 | 25.7 |
| 15.75 | 13 |
| 16.53 | 19.7 |
| 17.29 | 23.6 |
| 19.31 | 100 |
| 19.78 | 55.1 |
| 20.10 | 99.5 |
| 20.60 | 40.5 |
| 21.01 | 20.5 |
| 21.68 | 82.3 |
| 22.45 | 13.5 |
| 23.22 | 21.8 |
| 23.58 | 33.8 |
| 23.98 | 20.8 |
| 24.30 | 14.8 |
| 24.65 | 16.1 |
| 25.56 | 27.8 |
| 25.83 | 52.5 |
| 26.37 | 35.6 |
| 27.98 | 38.4 |
| 28.44 | 34.3 |
| 28.91 | 16.9 |
| 29.72 | 29.6 |
| 30.34 | 13 |
| 32.72 | 14.5 |
| 36.21 | 22.3 |
| 38.18 | 11.9 |

As stated above, it is known in the art that an X-ray powder diffraction pattern may be obtained which has one or more measurement errors depending on measurement conditions (such as equipment, sample preparation or machine used). In particular, it is generally known that intensities in an X-ray powder diffraction pattern may fluctuate depending on measurement conditions and sample preparation. For example, persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern data presented herein is not to be construed as absolute (for further information see Jenkins, R & Snyder, R. L. 'Introduction to X-Ray Powder Diffractometry' John Wiley & Sons, 1996).

It is also stated above that, in general, a measurement error of a diffraction angle in an X-ray powder diffractogram is about 2-theta=0.5° or less (or, more suitably, about 2-theta=0.2° or less) and such degree of a measurement error should be taken into account when considering the X-ray powder diffraction pattern in FIG. 1, and when interpreting the peak positions referred to in the text above and in Table 1.

With this in mind, a person skilled in the art will appreciate that the data presented in FIG. 7 and Table 2 above indicate that the maleate co-crystal of AZD1152 produced by Method 2 is the same crystalline form as the maleate co-crystal of AZD1152 produced by Method 1 (and shown in FIG. 1 and Table 1).

The invention claimed is:

1. A crystalline form of the maleate co-crystal of 2-{ethyl [3-({4-[(5-{2-[(3-fluorophenyl)amino]-2-oxoethyl}-1H-pyrazol-3-yl)amino]quinazolin-7-yl}oxy)propyl]amino}ethyl dihydrogen phosphate, wherein said co-crystal has an X-ray powder diffraction pattern with specific peaks at about 12.9°, 15.2° and/or 10.2°.

2. A pharmaceutical composition comprising a maleate co-crystal of 2-{ethyl[3-({4-[(5-{2-[(3-fluorophenyl)amino]-2-oxoethyl}-1H-pyrazol-3-yl)amino]quinazolin-7yl}oxy)propyl]amino}ethyl dihydrogen phosphate, as defined in claim 1 in association with a pharmaceutically acceptable diluent or carrier.

3. A crystalline form according to claim 1 having an X-ray powder diffraction pattern with specific peaks at about 2-theta=12.9° and 15.2° and 10.2°.

4. A crystalline form according to claim 1 having an X-ray powder diffraction pattern with a specific peak at about 2-theta=18.1°.

5. A crystalline form according to claim 3 having an X-ray powder diffraction pattern with a specific peak at about 2-theta=18.1°.

6. A crystalline form according to claim 5 having an x-ray powder diffraction pattern substantially the same as the X-ray powder diffraction pattern shown in FIG. 1.

* * * * *

SEQUENCE LISTING

<160> NUMBER OF SEQ ID NOS: 3

<210> SEQ ID NO 1
<211> LENGTH: 33
<212> TYPE: DNA
<213> ORGANISM: Artificial
<220> FEATURE:
<223> OTHER INFORMATION: The aurora2 coding sequence followed by a stop
      codon and a recognition sequence for the restriction endonuclease
      Not1

<400> SEQUENCE: 1
tacccatacg atgttccaga ttacgcttct taa                               33

<210> SEQ ID NO 2
<211> LENGTH: 10
<212> TYPE: PRT
<213> ORGANISM: Artificial
<220> FEATURE:
<223> OTHER INFORMATION: Aurora2 polypeptide sequence

<400> SEQUENCE: 2

Tyr Pro Tyr Asp Val Pro Asp Tyr Ala Ser
1               5                   10

<210> SEQ ID NO 3
<211> LENGTH: 28
<212> TYPE: PRT
<213> ORGANISM: Artificial
<220> FEATURE:
<223> OTHER INFORMATION: Aurora2 peptide substrate

<400> SEQUENCE: 3

Leu Arg Arg Trp Ser Leu Gly Leu Arg Arg Trp Ser Leu Gly Leu Arg
1               5                   10                  15

Arg Trp Ser Leu Gly Leu Arg Arg Trp Ser Leu Gly
            20                  25